United States Patent
McGaff

(10) Patent No.: US 10,065,980 B2
(45) Date of Patent: Sep. 4, 2018

(54) BRIDGED PHTHALOCYANINE- AND NAPTHTHALOCYANINE-METAL COMPLEX CATALYSTS AND METHODS OF USING AND PURIFYING THE SAME

(71) Applicant: WiSys Technology Foundation, Inc., Madison, WI (US)

(72) Inventor: Robert William McGaff, LaCrosse, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 0 days.

(21) Appl. No.: 15/217,350

(22) Filed: Jul. 22, 2016

(65) Prior Publication Data

US 2017/0022233 A1    Jan. 26, 2017

Related U.S. Application Data

(60) Provisional application No. 62/312,938, filed on Mar. 24, 2016, provisional application No. 62/196,763, filed on Jul. 24, 2015.

(51) Int. Cl.
| | | |
|---|---|---|
| *C07F 15/02* | (2006.01) | |
| *C07C 45/29* | (2006.01) | |
| *C07D 307/48* | (2006.01) | |
| *B01J 31/18* | (2006.01) | |

(52) U.S. Cl.
CPC ......... *C07F 15/025* (2013.01); *B01J 31/1835* (2013.01); *C07C 45/29* (2013.01); *C07C 45/294* (2013.01); *C07D 307/48* (2013.01); *B01J 2231/763* (2013.01); *B01J 2531/842* (2013.01); *C07C 2601/14* (2017.05)

(58) Field of Classification Search
CPC .... B01J 31/1835; C07C 45/29; C07C 45/294; C07C 307/48; C07F 15/025
See application file for complete search history.

(56) References Cited

PUBLICATIONS

Kieler et al., "Racemic iron(III) and cobalt(III) complexes containing a new pentadentate "helmet" phthalocyaninato ligand," Chem. Comm. 2006, 3326-3328.*
Kieler, Heidi M., et al., "Racemic iron(III) and cobalt(III) complexes containing a new pentadentate "helmet" phthalocyaninato ligand", *Chem. Commun.*, (2006), 3326-3328.
Kikukawa, Yuu, et al., "Facile one-pot preparation of thermally and photochemically convertible soluble precursors of copper phthalocyanine and naphthalocyanine", *Chem. Commun.*, 47, (2011), 8518-8520.
Peterson, Brian M., et al., "Oxidation of primary and secondary benzylic alcohols with hydrogen peroxide and tert-butyl hydroperoxide catalyzed by a "helmet" phthalocyaninato iron complex in the absence of added organic solvent", *Dalton Trans.*, 43, (2014), 17899-17903.

* cited by examiner

*Primary Examiner* — Pancham Bakshi
*Assistant Examiner* — Mark R Luderer
(74) *Attorney, Agent, or Firm* — Schwegman Lundberg & Woessner, P.A.

(57) ABSTRACT

Various embodiments disclosed relate to bridged phthalocyanine- and napththalocyanine-metal complex catalysts and methods of using and purifying the same. In various embodiments, the present invention provides a method of purifying a catalyst. The method includes contacting a catalyst composition with acid, the catalyst composition including a catalyst, to provide an acidified catalyst composition with the catalyst dissolved therein. The method includes precipitating the catalyst, and removing the precipitated catalyst from solution, to provide a purified catalyst.

19 Claims, 22 Drawing Sheets

Table 2: Crystal data and structure refinement for 2.

| Empirical formula | $C_{40}H_{22}FeN_{11}O \cdot 3EtOH$ |
|---|---|
| Formula weight | 866.74 |
| Temperature/K | 100.04 |
| Crystal system | monoclinic |
| Space group | $P2_1/n$ |
| a/Å | 15.200(4) |
| b/Å | 13.875(4) |
| c/Å | 19.210(5) |
| α/° | 90 |
| β/° | 104.532(11) |
| γ/° | 90 |
| Volume/Å$^3$ | 3922(2) |
| Z | 4 |
| $\rho_{calc}$g/cm$^3$ | 1.468 |
| μ/mm$^{-1}$ | 0.448 |
| F(000) | 1804.0 |
| Crystal size/mm$^3$ | 0.08 × 0.08 × 0.08 |
| Radiation | MoKα (λ = 0.71073) |
| 2Θ range for data collection/° | 3.068 to 61.142 |
| Index ranges | $-21 \leq h \leq 21, -19 \leq k \leq 19, -27 \leq l \leq 27$ |
| Reflections collected | 111776 |
| Independent reflections | 12032 [$R_{int}$ = 0.0541, $R_{sigma}$ = 0.0290] |
| Data/restraints/parameters | 12032/10/577 |
| Goodness-of-fit on F$^2$ | 1.040 |
| Final R indexes [I>=2σ (I)] | $R_1$ = 0.0374, $wR_2$ = 0.0892 |
| Final R indexes [all data] | $R_1$ = 0.0505, $wR_2$ = 0.0969 |
| Largest diff. peak/hole / e Å$^{-3}$ | 0.62/-0.54 |

FIG. 4A

Table 3: Fractional atomic coordinates (×10$^4$) and equivalent isotropic displacement parameters (Å$^2$×10$^3$) for 2. U$_{eq}$ is defined as 1/3 of the trace of the orthogonalised U$_{IJ}$ tensor.

| ATOM | x | y | z | U(EQ) |
|---|---|---|---|---|
| Fe1 | 5484.3(2) | 4543.7(2) | 7614.1(2) | 7.74(5) |
| O1 | 5781.8(7) | 3161.5(7) | 7629.3(6) | 12.15(19) |
| N1 | 5958.0(8) | 4600.3(8) | 6782.2(6) | 10.3(2) |
| N2 | 4697.2(8) | 3874.0(9) | 5923.5(7) | 12.1(2) |
| N3 | 4329.6(8) | 4310.9(8) | 7025.8(6) | 8.9(2) |
| N4 | 3427.1(8) | 4291.8(8) | 7937.5(6) | 10.5(2) |
| N5 | 5047.8(8) | 4373.7(8) | 8451.4(6) | 9.2(2) |
| N6 | 6479.6(8) | 4381.1(8) | 9352.5(6) | 10.9(2) |
| N7 | 6608.2(8) | 4923.7(8) | 8199.1(6) | 9.4(2) |
| N8 | 7457.9(8) | 5248.5(9) | 7291.2(7) | 11.7(2) |
| N9 | 3528.8(8) | 5731.3(8) | 7255.5(6) | 10.0(2) |
| N10 | 5169.9(8) | 5847.4(8) | 7541.2(6) | 9.3(2) |
| N11 | 6671.4(8) | 6534.9(8) | 7708.3(6) | 10.1(2) |
| C1 | 6866.7(9) | 4807.1(10) | 6798.9(8) | 11.0(2) |
| C2 | 7034.9(10) | 4453.9(10) | 6118.4(8) | 12.6(3) |
| C3 | 7806.6(10) | 4465.3(11) | 5859.8(8) | 15.4(3) |
| C4 | 7730.5(11) | 4093.3(11) | 5172.6(9) | 19.1(3) |
| C5 | 6907.7(12) | 3730.7(12) | 4759.9(9) | 19.0(3) |
| C6 | 6134.3(11) | 3721.1(11) | 5025.1(8) | 16.5(3) |
| C7 | 6214(1) | 4082(1) | 5710.2(8) | 12.8(3) |
| C8 | 5548.4(10) | 4171.3(10) | 6150.1(8) | 11.5(2) |
| C9 | 4119.7(9) | 4050.9(10) | 6346.7(8) | 10.6(2) |
| C10 | 3125.9(10) | 3973.2(10) | 6085.2(8) | 11.4(2) |
| C11 | 2591.5(10) | 3590.5(11) | 5456.2(8) | 14.4(3) |
| C12 | 1661.5(10) | 3527.8(11) | 5391.7(8) | 16.3(3) |
| C13 | 1286(1) | 3874.4(11) | 5932.8(8) | 15.7(3) |
| C14 | 1826.9(10) | 4292.9(10) | 6555.5(8) | 13.1(3) |
| C15 | 2753.6(9) | 4318.9(10) | 6628.5(7) | 10.3(2) |
| C16 | 3525.9(9) | 4658.2(9) | 7247.6(7) | 9.2(2) |
| C17 | 4142.1(9) | 4182.5(9) | 8453.9(7) | 9.4(2) |
| C18 | 4139.6(9) | 3844.1(10) | 9184.8(7) | 10.5(2) |
| C19 | 3446.8(10) | 3546.5(10) | 9484.6(8) | 12.7(3) |
| C20 | 3682.7(10) | 3248.8(10) | 10201.8(8) | 14.3(3) |
| C21 | 4583.5(10) | 3268.9(11) | 10606.3(8) | 14.5(3) |
| C22 | 5278.9(10) | 3588.3(10) | 10307.2(8) | 12.8(3) |

FIG. 4B

Table 3 CONTINUED: Fractional atomic coordinates ($\times 10^4$) and equivalent isotropic displacement parameters ($Å^2 \times 10^3$) for 2. $U_{eq}$ is defined as 1/3 of the trace of the orthogonalised $U_{IJ}$ tensor.

| Atom | x | y | z | U(eq) |
|---|---|---|---|---|
| C23 | 5040.4(9) | 3865.4(10) | 9592.0(7) | 10.6(2) |
| C24 | 5596.4(9) | 4221.1(9) | 9116.9(7) | 9.8(2) |
| C25 | 6907.8(9) | 4830.4(10) | 8897.8(8) | 10.2(2) |
| C26 | 7785.5(9) | 5329.6(10) | 9147.8(8) | 11.4(2) |
| C27 | 8370.5(10) | 5405.6(11) | 9828.8(8) | 14.7(3) |
| C28 | 9148.7(10) | 5965.3(11) | 9895.8(9) | 17.6(3) |
| C29 | 9322.4(10) | 6433.7(11) | 9301.9(9) | 17.0(3) |
| C31 | 7958.3(9) | 5797(1) | 8555.3(8) | 11.2(2) |
| C32 | 7163.4(9) | 5612.9(10) | 7910.0(8) | 10.3(2) |
| C33 | 4291.1(9) | 6196.2(10) | 7364.4(7) | 9.5(2) |
| C34 | 4350.6(9) | 7253.7(10) | 7278.3(7) | 10.4(2) |
| C35 | 3678(1) | 7947.5(10) | 7071.6(8) | 13.0(3) |
| C36 | 3955.6(10) | 8889.6(10) | 6985.9(8) | 15.1(3) |
| C37 | 4875.1(11) | 9127.7(10) | 7119.5(8) | 15.6(3) |
| C38 | 5549.9(10) | 8431.3(10) | 7336.8(8) | 13.5(3) |
| C39 | 5271.0(9) | 7491.7(10) | 7401.4(7) | 10.3(2) |
| C40 | 5793.3(9) | 6578.9(9) | 7570.0(7) | 9.7(2) |
| O2 | 7491.5(7) | 2751.3(8) | 8067.2(6) | 14.5(2) |
| C41 | 7758.6(10) | 2393.3(11) | 8789.0(8) | 15.0(3) |
| C42 | 8735.6(12) | 2636.4(18) | 9142.7(10) | 33.5(5) |
| O3 | 4677.2(8) | 2015.3(10) | 8083.4(7) | 26.9(3) |
| C43 | 5017.0(11) | 1239.4(12) | 8559.8(9) | 19.6(3) |
| C44 | 4550.4(11) | 1215.8(12) | 9166.8(9) | 19.8(3) |
| O4 | 3053.4(8) | 1322.1(9) | 7371.0(6) | 20.6(2) |
| C45 | 2742.4(11) | 1433.4(12) | 6609.8(9) | 19.5(3) |
| C46 | 3557.6(12) | 1511.5(12) | 6295.2(9) | 21.4(3) |

FIG. 4C

Table 4: Anisotropic displacement parameters ($Å^2 \times 10^3$) for 2. The anisotropic displacement factor exponent takes the form: $-2\pi2[h2a*2U11+2hka*b*U12+...]$.

| Atom | $U_{11}$ | $U_{22}$ | $U_{33}$ | $U_{23}$ | $U_{13}$ | $U_{12}$ |
|---|---|---|---|---|---|---|
| Fe1 | 6.80(9) | 7.82(9) | 8.68(9) | 0.08(6) | 2.10(7) | 0.36(6) |
| O1 | 8.9(5) | 10.2(4) | 17.7(5) | 1.0(4) | 4.1(4) | 0.8(3) |
| N1 | 8.7(5) | 11.7(5) | 10.8(5) | -0.4(4) | 3.1(4) | 0.4(4) |
| N2 | 11.3(5) | 13.5(5) | 12.0(6) | -1.7(4) | 3.8(4) | -0.1(4) |
| N3 | 7.8(5) | 8.7(5) | 10.3(5) | 0.2(4) | 2.6(4) | 0.6(4) |
| N4 | 10.1(5) | 11.2(5) | 10.7(5) | 0.6(4) | 3.8(4) | 0.3(4) |
| N5 | 7.3(5) | 10.3(5) | 10.0(5) | 0.9(4) | 2.3(4) | -0.3(4) |
| N6 | 9.8(5) | 10.8(5) | 11.4(5) | 1.2(4) | 1.6(4) | -0.6(4) |
| N7 | 7.3(5) | 8.5(5) | 12.6(5) | 0.5(4) | 2.9(4) | 0.4(4) |
| N8 | 11.0(5) | 11.4(5) | 14.0(6) | 0.5(4) | 5.4(5) | 0.7(4) |
| N9 | 9.9(5) | 10.1(5) | 10.2(5) | -0.2(4) | 2.6(4) | 1.0(4) |
| N10 | 7.9(5) | 9.3(5) | 10.6(5) | 0.4(4) | 2.3(4) | 0.3(4) |
| N11 | 10.0(5) | 9.5(5) | 10.9(5) | 0.6(4) | 2.7(4) | 0.1(4) |
| C1 | 10.8(6) | 10.4(6) | 13.2(6) | 1.8(5) | 5.6(5) | 1.4(5) |
| C2 | 14.2(6) | 11.8(6) | 13.3(6) | 0.8(5) | 6.4(5) | 1.1(5) |
| C3 | 14.3(7) | 15.8(6) | 18.6(7) | -0.4(5) | 8.6(6) | -0.9(5) |
| C4 | 21.1(8) | 19.4(7) | 21.3(8) | -0.5(6) | 13.9(6) | 1.4(6) |
| C5 | 25.0(8) | 19.5(7) | 15.7(7) | -2.5(6) | 11.3(6) | 0.6(6) |
| C6 | 18.7(7) | 17.7(7) | 14.5(7) | -2.2(5) | 6.6(6) | -0.8(5) |
| C7 | 13.6(6) | 13.0(6) | 13.5(7) | 0.7(5) | 6.4(5) | 1.2(5) |
| C8 | 13.0(6) | 10.9(6) | 11.3(6) | 0.6(5) | 4.4(5) | 1.3(5) |
| C9 | 11.0(6) | 9.4(6) | 11.3(6) | 0.5(4) | 2.7(5) | 0.5(4) |
| C10 | 10.6(6) | 11.5(6) | 11.8(6) | 0.9(5) | 2.1(5) | 0.3(5) |
| C11 | 14.7(7) | 15.1(6) | 12.4(7) | -1.4(5) | 1.6(5) | 0.1(5) |
| C12 | 14.2(7) | 16.8(7) | 14.4(7) | -1.5(5) | -3.2(5) | -1.5(5) |
| C13 | 10.0(6) | 16.9(7) | 18.1(7) | 1.3(5) | -0.5(5) | -1.6(5) |
| C14 | 10.7(6) | 14.3(6) | 13.9(7) | 0.8(5) | 2.1(5) | 0.1(5) |
| C15 | 9.9(6) | 9.8(5) | 10.4(6) | 1.0(4) | 0.8(5) | -0.2(4) |
| C16 | 7.4(6) | 10.4(6) | 9.7(6) | 0.1(4) | 2.0(5) | 0.3(4) |
| C17 | 10.4(6) | 7.5(5) | 11.2(6) | -0.6(4) | 4.2(5) | 0.0(4) |
| C18 | 12.0(6) | 9.2(6) | 10.7(6) | -0.6(4) | 3.8(5) | 0.6(5) |
| C19 | 11.9(6) | 13.3(6) | 13.7(7) | -1.1(5) | 4.6(5) | 0.0(5) |
| C20 | 17.5(7) | 13.9(6) | 13.7(7) | -0.1(5) | 8.1(6) | -0.6(5) |
| C21 | 19.3(7) | 14.6(6) | 10.6(6) | 0.4(5) | 5.4(5) | 0.1(5) |
| C22 | 14.1(6) | 12.7(6) | 10.9(6) | -0.5(5) | 1.9(5) | 0.0(5) |

FIG. 4D

Table 4 CONTINUED: Anisotropic displacement parameters ($Å^2 \times 10^3$) for 2. The anisotropic displacement factor exponent takes the form: $-2\pi^2[h^2 a^{*2} U_{11} + 2hk a^* b^* U_{12} + ...]$.

| Atom | $U_{11}$ | $U_{22}$ | $U_{33}$ | $U_{23}$ | $U_{13}$ | $U_{12}$ |
|---|---|---|---|---|---|---|
| C23 | 11.1(6) | 9.8(6) | 11.3(6) | -0.4(5) | 3.5(5) | -0.7(4) |
| C24 | 11.0(6) | 8.1(5) | 10.2(6) | 0.3(4) | 2.8(5) | 0.7(4) |
| C25 | 8.7(6) | 8.5(5) | 12.9(6) | 0.2(4) | 1.9(5) | 1.1(4) |
| C26 | 8.5(6) | 10.7(6) | 14.6(6) | 0.3(5) | 2.0(5) | -0.5(5) |
| C27 | 12.7(6) | 16.4(6) | 13.7(7) | 1.1(5) | 1.1(5) | -0.5(5) |
| C28 | 12.3(7) | 20.9(7) | 17.3(7) | -0.9(6) | -0.8(6) | -2.9(5) |
| C29 | 10.3(6) | 18.5(7) | 21.2(8) | -1.2(6) | 2.1(6) | -4.4(5) |
| C31 | 8.8(6) | 11.3(6) | 13.4(6) | -0.6(5) | 2.4(5) | 1.1(5) |
| C32 | 8.8(6) | 9.6(6) | 12.8(6) | 0.8(5) | 3.3(5) | -0.1(4) |
| C33 | 10.4(6) | 10.4(6) | 7.9(6) | 0.3(4) | 2.7(5) | 1.7(4) |
| C34 | 11.9(6) | 10.0(6) | 9.4(6) | 0.0(4) | 3.0(5) | 1.5(5) |
| C35 | 12.4(6) | 12.4(6) | 14.4(7) | 0.6(5) | 3.6(5) | 2.2(5) |
| C36 | 17.0(7) | 12.0(6) | 16.1(7) | 2.4(5) | 4.1(6) | 5.0(5) |
| C37 | 20.4(7) | 9.6(6) | 17.8(7) | 1.6(5) | 6.9(6) | 1.2(5) |
| C38 | 14.9(7) | 11.8(6) | 14.5(7) | -0.4(5) | 5.3(5) | -0.7(5) |
| C39 | 11.4(6) | 11.0(6) | 8.8(6) | 0.2(4) | 2.9(5) | 1.7(5) |
| C40 | 11.2(6) | 10.1(6) | 8.1(6) | -0.1(4) | 2.9(5) | 0.0(5) |
| O2 | 12.8(5) | 17.1(5) | 13.7(5) | -0.2(4) | 3.8(4) | 4.4(4) |
| C41 | 13.4(7) | 17.8(7) | 13.9(7) | -0.3(5) | 3.8(5) | 1.4(5) |
| C42 | 17.9(8) | 64.6(14) | 16.6(8) | 6.2(8) | 1.5(7) | -6.9(8) |
| O3 | 16.4(6) | 34.8(7) | 26.0(7) | 12.4(5) | -1.1(5) | -10.6(5) |
| C43 | 17.3(7) | 22.6(7) | 18.0(7) | 0.5(6) | 2.7(6) | -0.8(6) |
| C44 | 21.0(8) | 19.3(7) | 18.4(8) | -0.6(6) | 3.9(6) | -4.0(6) |
| O4 | 11.5(5) | 30.9(6) | 19.0(6) | 6.6(5) | 3.1(4) | -5.0(4) |
| C45 | 15.5(7) | 21.0(7) | 20.8(8) | 5.9(6) | 2.1(6) | 0.2(6) |
| C46 | 26.2(8) | 16.3(7) | 24.0(8) | 4.5(6) | 10.5(7) | 3.0(6) |

FIG. 4E

Table 5: Bond lengths for 2.

| Atom | Atom | Length/Å | Atom | Atom | Length/Å |
|---|---|---|---|---|---|
| Fe1 | O1 | 1.9689(12) | C10 | C11 | 1.382(2) |
| Fe1 | N1 | 1.9119(13) | C10 | C15 | 1.391(2) |
| Fe1 | N3 | 1.8618(13) | C11 | C12 | 1.390(2) |
| Fe1 | N5 | 1.9022(13) | C12 | C13 | 1.391(2) |
| Fe1 | N7 | 1.8698(13) | C13 | C14 | 1.396(2) |
| Fe1 | N10 | 1.8673(13) | C14 | C15 | 1.381(2) |
| N1 | C1 | 1.4032(18) | C15 | C16 | 1.5210(19) |
| N1 | C8 | 1.3553(18) | C17 | C18 | 1.4815(19) |
| N2 | C8 | 1.3232(19) | C18 | C19 | 1.3841(19) |
| N2 | C9 | 1.3601(18) | C18 | C23 | 1.396(2) |
| N3 | C9 | 1.3134(18) | C19 | C20 | 1.396(2) |
| N3 | C16 | 1.4721(17) | C20 | C21 | 1.395(2) |
| N4 | C16 | 1.4620(18) | C21 | C22 | 1.396(2) |
| N4 | C17 | 1.2834(18) | C22 | C23 | 1.385(2) |
| N5 | C17 | 1.4032(18) | C23 | C24 | 1.4758(19) |
| N5 | C24 | 1.3564(18) | C25 | C26 | 1.4726(19) |
| N6 | C24 | 1.3233(18) | C26 | C27 | 1.389(2) |
| N6 | C25 | 1.3642(18) | C26 | C31 | 1.391(2) |
| N7 | C25 | 1.3109(19) | C27 | C28 | 1.394(2) |
| N7 | C32 | 1.4732(17) | C28 | C29 | 1.395(2) |
| N8 | C1 | 1.2847(19) | C29 | C30 | 1.396(2) |
| N8 | C32 | 1.4615(18) | C30 | C31 | 1.383(2) |
| N9 | C16 | 1.4890(18) | C31 | C32 | 1.520(2) |
| N9 | C33 | 1.2964(18) | C33 | C34 | 1.4819(19) |
| N10 | C33 | 1.3806(18) | C34 | C35 | 1.3878(19) |
| N10 | C40 | 1.3801(18) | C34 | C39 | 1.398(2) |
| N11 | C32 | 1.4833(18) | C35 | C36 | 1.396(2) |
| N11 | C40 | 1.2953(18) | C36 | C37 | 1.396(2) |
| C1 | C2 | 1.477(2) | C37 | C38 | 1.395(2) |
| C2 | C3 | 1.384(2) | C38 | C39 | 1.3862(19) |
| C2 | C7 | 1.395(2) | C39 | C40 | 1.4867(19) |
| C3 | C4 | 1.395(2) | O2 | C41 | 1.4324(18) |
| C4 | C5 | 1.396(2) | C41 | C42 | 1.508(2) |
| C5 | C6 | 1.394(2) | O3 | C43 | 1.423(2) |
| C6 | C7 | 1.385(2) | C43 | C44 | 1.510(2) |
| C7 | C8 | 1.477(2) | O4 | C45 | 1.428(2) |
| C9 | C10 | 1.471(2) | C45 | C46 | 1.513(2) |

FIG. 4F

Table 6: Bond angles for 2.

| Atom | Atom | Atom | Angle/° | Atom | Atom | Atom | Angle/° |
|---|---|---|---|---|---|---|---|
| N1 | Fe1 | O1 | 85.36(5) | C14 | C15 | C10 | 120.76(13) |
| N3 | Fe1 | O1 | 91.04(5) | C14 | C15 | C16 | 130.93(13) |
| N3 | Fe1 | N1 | 89.72(6) | N3 | C16 | N9 | 109.25(11) |
| N3 | Fe1 | N5 | 90.92(5) | N3 | C16 | C15 | 101.89(11) |
| N3 | Fe1 | N7 | 173.57(5) | N4 | C16 | N3 | 115.47(11) |
| N3 | Fe1 | N10 | 86.45(5) | N4 | C16 | N9 | 109.83(11) |
| N5 | Fe1 | O1 | 89.67(5) | N4 | C16 | C15 | 111.50(11) |
| N5 | Fe1 | N1 | 175.00(5) | N9 | C16 | C15 | 108.49(11) |
| N7 | Fe1 | O1 | 95.39(5) | N4 | C17 | N5 | 128.04(13) |
| N7 | Fe1 | N1 | 90.68(6) | N4 | C17 | C18 | 124.54(13) |
| N7 | Fe1 | N5 | 89.23(5) | N5 | C17 | C18 | 107.40(12) |
| N10 | Fe1 | O1 | 176.59(5) | C19 | C18 | C17 | 132.23(13) |
| N10 | Fe1 | N1 | 92.32(5) | C19 | C18 | C23 | 120.98(13) |
| N10 | Fe1 | N5 | 92.66(5) | C23 | C18 | C17 | 106.79(12) |
| N10 | Fe1 | N7 | 87.12(5) | C18 | C19 | C20 | 117.71(14) |
| C1 | N1 | Fe1 | 124.35(10) | C21 | C20 | C19 | 121.13(14) |
| C8 | N1 | Fe1 | 123.10(10) | C20 | C21 | C22 | 121.06(14) |
| C8 | N1 | C1 | 109.79(12) | C23 | C22 | C21 | 117.38(14) |
| C8 | N2 | C9 | 118.13(13) | C18 | C23 | C24 | 107.08(12) |
| C9 | N3 | Fe1 | 127.42(10) | C22 | C23 | C18 | 121.72(13) |
| C9 | N3 | C16 | 111.41(11) | C22 | C23 | C24 | 131.20(13) |
| C16 | N3 | Fe1 | 119.46(9) | N5 | C24 | C23 | 108.86(12) |
| C17 | N4 | C16 | 118.82(12) | N6 | C24 | N5 | 128.84(13) |
| C17 | N5 | Fe1 | 125.24(9) | N6 | C24 | C23 | 122.26(13) |
| C24 | N5 | Fe1 | 123.64(10) | N6 | C25 | C26 | 123.01(13) |
| C24 | N5 | C17 | 109.81(11) | N7 | C25 | N6 | 126.99(13) |
| C24 | N6 | C25 | 117.63(12) | N7 | C25 | C26 | 109.94(12) |
| C25 | N7 | Fe1 | 128.16(10) | C27 | C26 | C25 | 131.02(13) |
| C25 | N7 | C32 | 111.43(11) | C27 | C26 | C31 | 121.84(13) |
| C32 | N7 | Fe1 | 118.67(9) | C31 | C26 | C25 | 107.09(12) |
| C1 | N8 | C32 | 117.59(12) | C26 | C27 | C28 | 117.21(14) |
| C33 | N9 | C16 | 119.96(11) | C27 | C28 | C29 | 120.97(14) |
| C33 | N10 | Fe1 | 124.86(9) | C28 | C29 | C30 | 121.35(14) |
| C40 | N10 | Fe1 | 123.31(9) | C31 | C30 | C29 | 117.54(14) |
| C40 | N10 | C33 | 111.36(11) | C26 | C31 | C32 | 108.32(12) |
| C40 | N11 | C32 | 121.34(11) | C30 | C31 | C26 | 121.09(14) |
| N1 | C1 | C2 | 107.45(12) | C30 | C31 | C32 | 130.49(13) |

FIG. 4G

Table 6 CONTINUED: Bond angles for 2.

| Atom | Atom | Atom | Angle/° | Atom | Atom | Atom | Angle/° |
|---|---|---|---|---|---|---|---|
| N8 | C1 | N1 | 128.10(13) | N7 | C32 | N11 | 111.06(11) |
| N8 | C1 | C2 | 124.41(13) | N7 | C32 | C31 | 102.40(11) |
| C3 | C2 | C1 | 131.63(14) | N8 | C32 | N7 | 113.79(11) |
| C3 | C2 | C7 | 121.43(14) | N8 | C32 | N11 | 108.85(11) |
| C7 | C2 | C1 | 106.92(12) | N8 | C32 | C31 | 112.24(11) |
| C2 | C3 | C4 | 117.32(14) | N11 | C32 | C31 | 108.28(11) |
| C3 | C4 | C5 | 121.37(14) | N9 | C33 | N10 | 129.47(13) |
| C6 | C5 | C4 | 120.90(15) | N9 | C33 | C34 | 123.49(12) |
| C7 | C6 | C5 | 117.60(15) | N10 | C33 | C34 | 106.99(12) |
| C2 | C7 | C8 | 106.96(13) | C35 | C34 | C33 | 131.11(13) |
| C6 | C7 | C2 | 121.36(14) | C35 | C34 | C39 | 121.24(13) |
| C6 | C7 | C8 | 131.68(14) | C39 | C34 | C33 | 107.54(12) |
| N1 | C8 | C7 | 108.83(12) | C34 | C35 | C36 | 117.41(13) |
| N2 | C8 | N1 | 128.54(13) | C37 | C36 | C35 | 121.22(13) |
| N2 | C8 | C7 | 122.62(13) | C38 | C37 | C36 | 121.22(13) |
| N2 | C9 | C10 | 122.96(13) | C39 | C38 | C37 | 117.39(14) |
| N3 | C9 | N2 | 127.66(13) | C34 | C39 | C40 | 107.01(12) |
| N3 | C9 | C10 | 109.39(12) | C38 | C39 | C34 | 121.49(13) |
| C11 | C10 | C9 | 130.88(13) | C38 | C39 | C40 | 131.47(13) |
| C11 | C10 | C15 | 121.87(13) | N10 | C40 | C39 | 107.10(12) |
| C15 | C10 | C9 | 107.13(12) | N11 | C40 | N10 | 129.44(13) |
| C10 | C11 | C12 | 117.60(14) | N11 | C40 | C39 | 123.46(12) |
| C11 | C12 | C13 | 120.69(14) | O2 | C41 | C42 | 111.49(13) |
| C12 | C13 | C14 | 121.33(14) | O3 | C43 | C44 | 110.37(14) |
| C15 | C14 | C13 | 117.67(14) | O4 | C45 | C46 | 108.84(13) |
| C10 | C15 | C16 | 108.29(12) | | | | |

FIG. 4H

Table 7: Hydrogen bonds for 2.

| D  | H   | A    | d(D-H)/Å   | d(H-A)/Å   | d(D-A)/Å   | D-H-A/°  |
|----|-----|------|------------|------------|------------|----------|
| O1 | H1A | O2   | 0.840(12)  | 1.749(12)  | 2.5860(16) | 174(2)   |
| O1 | H1B | O3   | 0.839(12)  | 1.777(12)  | 2.6161(16) | 178(2)   |
| O2 | H2  | N11[1] | 0.839(12) | 1.931(12)  | 2.7637(16) | 171(2)   |
| O3 | H3A | O4   | 0.843(12)  | 1.851(13)  | 2.6822(18) | 168(3)   |
| O4 | H4A | N9[2]  | 0.841(12) | 1.979(13)  | 2.7994(17) | 165(2)   |

FIG. 4I

Table 8: Torsion angles for 2.

| A | B | C | D | Angle/° | A | B | C | D | Angle/° |
|---|---|---|---|---|---|---|---|---|---|
| Fe1 | N1 | C1 | N8 | -21.8(2) | C10 | C11 | C12 | C13 | 2.4(2) |
| Fe1 | N1 | C1 | C2 | 160.38(9) | C10 | C15 | C16 | N3 | -8.94(14) |
| Fe1 | N1 | C8 | N2 | 18.8(2) | C10 | C15 | C16 | N4 | -132.67(12) |
| Fe1 | N1 | C8 | C7 | -161.99(9) | C10 | C15 | C16 | N9 | 106.25(13) |
| Fe1 | N3 | C9 | N2 | 1.4(2) | C11 | C10 | C15 | C14 | -0.2(2) |
| Fe1 | N3 | C9 | C10 | -178.38(9) | C11 | C10 | C15 | C16 | 178.35(13) |
| Fe1 | N3 | C16 | N4 | -58.92(14) | C11 | C12 | C13 | C14 | -0.1(2) |
| Fe1 | N3 | C16 | N9 | 65.44(13) | C12 | C13 | C14 | C15 | -2.4(2) |
| Fe1 | N3 | C16 | C15 | -179.92(8) | C13 | C14 | C15 | C10 | 2.5(2) |
| Fe1 | N5 | C17 | N4 | -16.6(2) | C13 | C14 | C15 | C16 | 175.66(14) |
| Fe1 | N5 | C17 | C18 | 164.93(9) | C14 | C15 | C16 | N3 | 169.38(14) |
| Fe1 | N5 | C24 | N6 | 17.6(2) | C14 | C15 | C16 | N4 | 45.7(2) |
| Fe1 | N5 | C24 | C23 | -164.93(9) | C14 | C15 | C16 | N9 | -75.43(18) |
| Fe1 | N7 | C25 | N6 | 4.0(2) | C15 | C10 | C11 | C12 | -2.3(2) |
| Fe1 | N7 | C25 | C26 | -173.40(9) | C16 | N3 | C9 | N2 | 166.26(13) |
| Fe1 | N7 | C32 | N8 | -63.36(13) | C16 | N3 | C9 | C10 | -13.56(15) |
| Fe1 | N7 | C32 | N11 | 59.88(13) | C16 | N4 | C17 | N5 | 0.0(2) |
| Fe1 | N7 | C32 | C31 | 175.27(8) | C16 | N4 | C17 | C18 | 178.27(12) |
| Fe1 | N10 | C33 | N9 | 4.2(2) | C16 | N9 | C33 | N10 | -5.9(2) |
| Fe1 | N10 | C33 | C34 | -173.05(9) | C16 | N9 | C33 | C34 | 170.94(12) |
| Fe1 | N10 | C40 | N11 | -6.6(2) | C17 | N4 | C16 | N3 | 37.74(17) |
| Fe1 | N10 | C40 | C39 | 173.00(9) | C17 | N4 | C16 | N9 | -86.31(14) |
| O1 | Fe1 | N3 | C9 | -70.42(12) | C17 | N4 | C16 | C15 | 153.39(12) |
| O1 | Fe1 | N3 | C16 | 125.85(10) | C17 | N5 | C24 | N6 | -174.89(13) |
| O1 | Fe1 | N7 | C25 | -76.03(12) | C17 | N5 | C24 | C23 | 2.60(15) |
| O1 | Fe1 | N7 | C32 | 120.37(10) | C17 | C18 | C19 | C20 | 178.77(14) |
| N1 | Fe1 | N3 | C9 | 14.94(12) | C17 | C18 | C23 | C22 | -179.87(13) |
| N1 | Fe1 | N3 | C16 | -148.79(10) | C17 | C18 | C23 | C24 | 0.36(14) |
| N1 | Fe1 | N7 | C25 | -161.44(12) | C18 | C19 | C20 | C21 | 1.3(2) |
| N1 | Fe1 | N7 | C32 | 34.96(10) | C18 | C23 | C24 | N5 | -1.82(15) |
| N1 | Fe1 | N10 | C33 | 111.52(11) | C18 | C23 | C24 | N6 | 175.87(13) |
| N1 | Fe1 | N10 | C40 | -59.98(11) | C19 | C18 | C23 | C22 | 0.3(2) |
| N1 | C1 | C2 | C3 | -179.45(15) | C19 | C18 | C23 | C24 | 179.51(12) |
| N1 | C1 | C2 | C7 | 2.13(15) | C19 | C20 | C21 | C22 | 0.1(2) |
| N2 | C9 | C10 | C11 | 11.2(2) | C20 | C21 | C22 | C23 | -1.2(2) |
| N2 | C9 | C10 | C15 | -172.66(13) | C21 | C22 | C23 | C18 | 1.0(2) |

FIG. 4J

Table 8 CONTINUED: Torsion angles for 2.

| A | B | C | D | Angle/° | A | B | C | D | Angle/° |
|---|---|---|---|---|---|---|---|---|---|
| N3 | Fe1 | N10 | C33 | 21.94(11) | C21 | C22 | C23 | C24 | 179.24(14) |
| N3 | Fe1 | N10 | C40 | -149.56(11) | C22 | C23 | C24 | N5 | 178.44(14) |
| N3 | C9 | C10 | C11 | -168.94(15) | C22 | C23 | C24 | N6 | -3.9(2) |
| N3 | C9 | C10 | C15 | 7.17(16) | C23 | C18 | C19 | C20 | -1.4(2) |
| N4 | C17 | C18 | C19 | 2.5(2) | C24 | N5 | C17 | N4 | 176.12(13) |
| N4 | C17 | C18 | C23 | 177.39(13) | C24 | N5 | C17 | C18 | -2.35(14) |
| N5 | Fe1 | N3 | C9 | 160.10(12) | C24 | N6 | C25 | N7 | -17.6(2) |
| N5 | Fe1 | N7 | C25 | 13.56(12) | C25 | N6 | C24 | N5 | 5.8(2) |
| N5 | Fe1 | N7 | C32 | -150.04(10) | C25 | N6 | C24 | C23 | 171.35(12) |
| N5 | Fe1 | N10 | C33 | -68.81(12) | C25 | N7 | C32 | N8 | 130.44(12) |
| N5 | Fe1 | N10 | C40 | 119.69(11) | C25 | N7 | C32 | N11 | -106.32(13) |
| N5 | C17 | C18 | C19 | -179.00(14) | C25 | N7 | C32 | C31 | 9.07(14) |
| N5 | C17 | C18 | C23 | 1.16(14) | C25 | C26 | C27 | C28 | -177.89(14) |
| N6 | C25 | C26 | C27 | 4.7(2) | C25 | C26 | C31 | C30 | 178.03(13) |
| N6 | C25 | C26 | C31 | 172.87(13) | C25 | C26 | C31 | C32 | 1.22(15) |
| N7 | Fe1 | N10 | C33 | 157.91(12) | C26 | C27 | C28 | C29 | 0.6(2) |
| N7 | Fe1 | N10 | C40 | 30.59(11) | C26 | C31 | C32 | N7 | -5.86(14) |
| N7 | C25 | C26 | C27 | -177.74(15) | C26 | C31 | C32 | N8 | -128.29(12) |
| N7 | C25 | C26 | C31 | 4.67(16) | C26 | C31 | C32 | N11 | 111.53(13) |
| N8 | C1 | C2 | C3 | 2.6(2) | C27 | C26 | C31 | C30 | 0.2(2) |
| N8 | C1 | C2 | C7 | 175.80(13) | C27 | C26 | C31 | C32 | 176.64(13) |
| N9 | C33 | C34 | C35 | -0.9(2) | C27 | C28 | C29 | C30 | -0.1(2) |
| N9 | C33 | C34 | C39 | 176.86(13) | C28 | C29 | C30 | C31 | -0.3(2) |
| N10 | Fe1 | N3 | C9 | 107.29(12) | C29 | C30 | C31 | C26 | 0.3(2) |
| N10 | Fe1 | N3 | C16 | -56.45(10) | C29 | C30 | C31 | C32 | 176.32(14) |
| N10 | Fe1 | N7 | C25 | 106.27(12) | C30 | C31 | C32 | N7 | 177.73(14) |
| N10 | Fe1 | N7 | C32 | -57.33(10) | C30 | C31 | C32 | N8 | 55.3(2) |
| N10 | C33 | C34 | C35 | 176.59(14) | C30 | C31 | C32 | N11 | -64.88(19) |
| N10 | C33 | C34 | C39 | 0.61(15) | C31 | C26 | C27 | C28 | -0.6(2) |
| C1 | N1 | C8 | N2 | -179.32(14) | C32 | N7 | C25 | N6 | 168.58(13) |
| C1 | N1 | C8 | C7 | -0.12(15) | C32 | N7 | C25 | C26 | -8.83(15) |
| C1 | N8 | C32 | N7 | 44.36(17) | C32 | N8 | C1 | N1 | -1.8(2) |
| C1 | N8 | C32 | N11 | -80.08(15) | C32 | N8 | C1 | C2 | 175.69(12) |
| C1 | N8 | C32 | C31 | 160.07(12) | C32 | N11 | C40 | N10 | -3.7(2) |
| C1 | C2 | C3 | C4 | -177.98(15) | C32 | N11 | C40 | C39 | 176.83(12) |
| C1 | C2 | C7 | C6 | 177.71(13) | C33 | N9 | C16 | N3 | -27.12(17) |
| C1 | C2 | C7 | C8 | -2.15(15) | C33 | N9 | C16 | N4 | 100.49(14) |
| C2 | C3 | C4 | C5 | 0.5(2) | C33 | N9 | C16 | C15 | -137.42(13) |

FIG. 4K

Table 8 CONTINUED: Torsion angles for 2.

| A | B | C | D | Angle/° | A | B | C | D | Angle/° |
|---|---|---|---|---|---|---|---|---|---|
| C2 | C7 | C8 | N1 | 1.48(16) | C33 | N10 | C40 | N11 | -179.09(14) |
| C2 | C7 | C8 | N2 | -179.26(13) | C33 | N10 | C40 | C39 | 0.48(15) |
| C3 | C2 | C7 | C6 | -0.9(2) | C33 | C34 | C35 | C36 | -175.01(14) |
| C3 | C2 | C7 | C8 | 179.23(13) | C33 | C34 | C39 | C38 | 177.81(13) |
| C3 | C4 | C5 | C6 | -0.6(2) | C33 | C34 | C39 | C40 | -0.32(15) |
| C4 | C5 | C6 | C7 | -0.1(2) | C34 | C35 | C36 | C37 | -1.5(2) |
| C5 | C6 | C7 | C2 | 0.8(2) | C34 | C39 | C40 | N10 | -0.08(15) |
| C5 | C6 | C7 | C8 | 179.38(15) | C34 | C39 | C40 | N11 | 179.53(13) |
| C6 | C7 | C8 | N1 | 178.36(15) | C35 | C34 | C39 | C38 | 1.4(2) |
| C6 | C7 | C8 | N2 | 0.9(2) | C35 | C34 | C39 | C40 | 176.78(13) |
| C7 | C2 | C3 | C4 | 0.2(2) | C35 | C36 | C37 | C38 | 0.6(2) |
| C8 | N1 | C1 | N8 | 176.61(14) | C36 | C37 | C38 | C39 | 1.2(2) |
| C8 | N1 | C1 | C2 | -1.21(15) | C37 | C38 | C39 | C34 | -2.2(2) |
| C8 | N2 | C9 | C10 | 164.76(13) | C38 | C39 | C40 | N10 | -177.95(14) |
| C9 | N2 | C8 | N1 | 3.8(2) | C38 | C39 | C40 | N11 | 1.7(2) |
| C9 | N2 | C8 | C7 | 175.34(13) | C39 | C34 | C35 | C36 | 0.5(2) |
| C9 | N3 | C16 | N4 | 134.90(12) | C40 | N10 | C33 | N9 | 176.59(14) |
| C9 | N3 | C16 | N9 | -100.74(13) | C40 | N10 | C33 | C34 | -0.67(15) |
| C9 | N3 | C16 | C15 | 13.90(14) | C40 | N11 | C32 | N7 | -22.33(18) |
| C9 | C10 | C11 | C12 | 173.31(14) | C40 | N11 | C32 | N8 | 103.71(14) |
| C9 | C10 | C15 | C14 | -176.70(13) | C40 | N11 | C32 | C31 | -134.02(13) |
| C9 | C10 | C15 | C16 | 1.82(15) | | | | | |

FIG. 4L

Table 9: Hydrogen atom coordinates (Å×10$^4$) and isotropic displacement parameters (Å$^2$×10$^3$) for 2.

| Atom | x | y | z | U(eq) |
|---|---|---|---|---|
| H1A | 6330(8) | 2995(14) | 7753(11) | 18 |
| H1B | 5435(12) | 2791(13) | 7781(10) | 18 |
| H3 | 8366 | 4716 | 6139 | 18 |
| H4 | 8250 | 4087 | 4982 | 23 |
| H5 | 6874 | 3487 | 4292 | 23 |
| H6 | 5573 | 3476 | 4746 | 20 |
| H11 | 2850 | 3378 | 5081 | 17 |
| H12 | 1278 | 3245 | 4974 | 20 |
| H13 | 649 | 3826 | 5878 | 19 |
| H14 | 1566 | 4551 | 6916 | 16 |
| H19 | 2832 | 3545 | 9212 | 15 |
| H20 | 3222 | 3029 | 10418 | 17 |
| H21 | 4726 | 3062 | 11093 | 17 |
| H22 | 5892 | 3615 | 10584 | 15 |
| H27 | 8245 | 5089 | 10232 | 18 |
| H28 | 9567 | 6029 | 10353 | 21 |
| H29 | 9857 | 6812 | 9362 | 20 |
| H30 | 8845 | 6680 | 8217 | 17 |
| H35 | 3053 | 7787 | 6992 | 16 |
| H36 | 3511 | 9378 | 6834 | 18 |
| H37 | 5044 | 9776 | 7061 | 19 |
| H38 | 6176 | 8595 | 7437 | 16 |
| H2 | 7708(13) | 2406(13) | 7792(10) | 22 |
| H41A | 7679 | 1685 | 8784 | 18 |
| H41B | 7361 | 2676 | 9072 | 18 |
| H42A | 9133 | 2324 | 8880 | 50 |
| H42B | 8889 | 2407 | 9641 | 50 |
| H42C | 8820 | 3336 | 9137 | 50 |
| H3A | 4139(10) | 1876(18) | 7865(12) | 40 |
| H43A | 5680 | 1317 | 8758 | 24 |
| H43B | 4911 | 623 | 8293 | 24 |
| H44A | 3896 | 1124 | 8970 | 30 |
| H44B | 4658 | 1825 | 9432 | 30 |
| H44C | 4794 | 682 | 9492 | 30 |
| H4A | 2610(12) | 1215(17) | 7548(12) | 31 |
| H45A | 2364 | 2021 | 6496 | 23 |
| H45B | 2366 | 872 | 6400 | 23 |
| H46A | 3351 | 1611 | 5775 | 32 |
| H46B | 3914 | 916 | 6392 | 32 |
| H46C | 3935 | 2058 | 6515 | 32 |

FIG. 4M

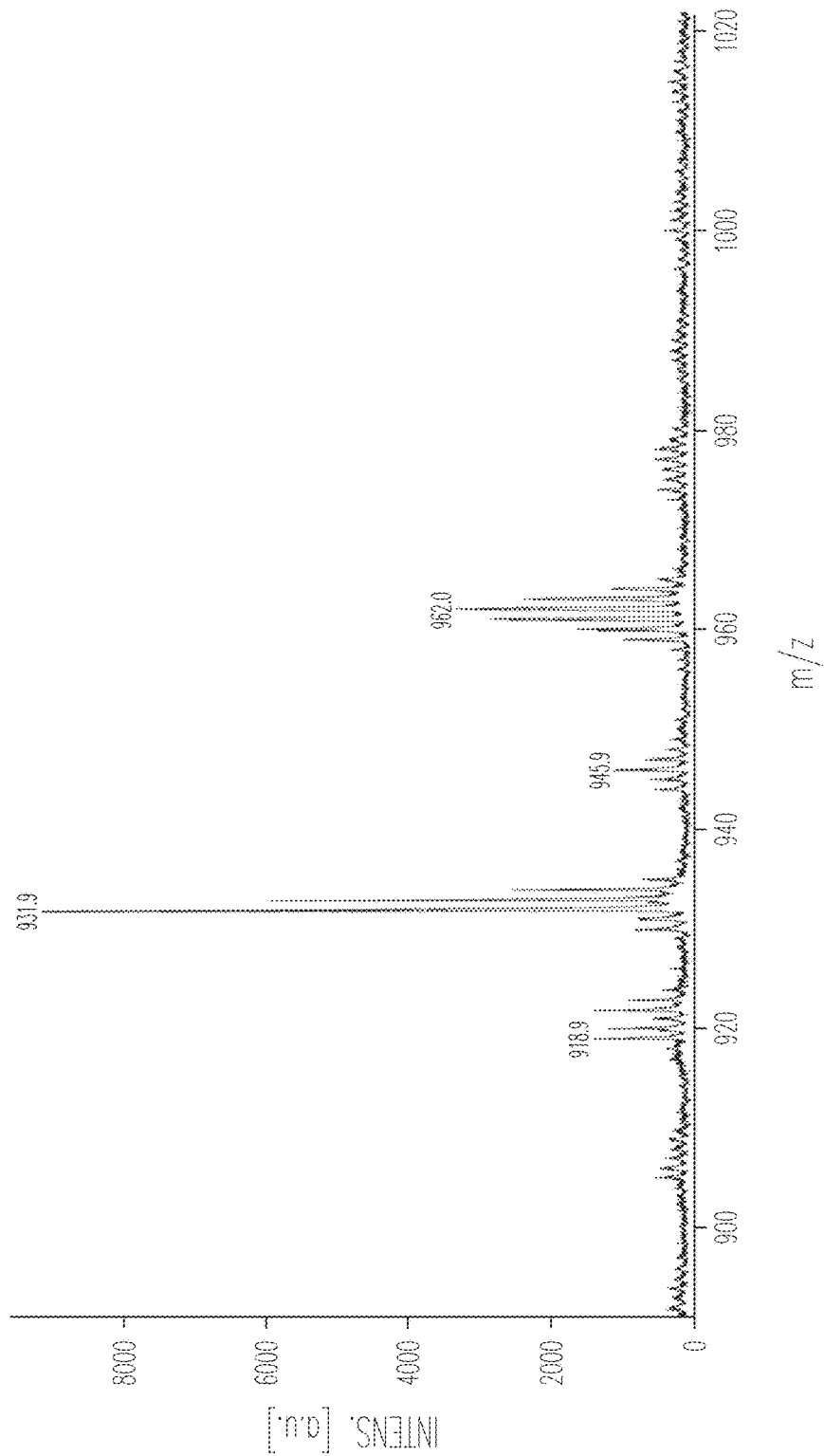

BRIDGED PHTHALOCYANINE- AND NAPHTHALOCYANINE-METAL COMPLEX CATALYSTS AND METHODS OF USING AND PURIFYING THE SAME

CROSS-REFERENCE TO RELATED APPLICATIONS

This application claims the benefit of priority to U.S. Provisional Patent Application Ser. No. 62/196,763 filed Jul. 24, 2015, and U.S. Provisional Patent Application Ser. No. 62/312,938, the disclosures of which are incorporated herein in their entirety by reference.

BACKGROUND

Oxidation reactions are extremely common and useful, such as oxidations of alcohols to ketones. However, most oxidation catalysts require addition of organic solvent, and require expensive and environmentally harmful heavy or precious metals, and environmentally harmful oxidants.

SUMMARY OF THE INVENTION

In various embodiments, the present invention provides a method of purifying a catalyst. The method includes contacting a catalyst composition with acid, the catalyst composition including a catalyst, to provide an acidified catalyst composition with the catalyst dissolved therein, the catalyst having the structure:

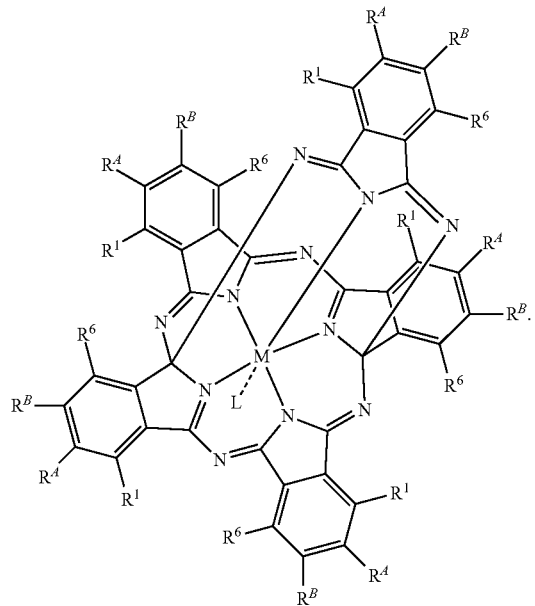

The variable M is a metal. Axial ligand L is a solvent molecule. At each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

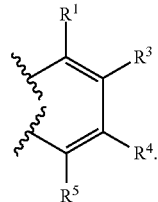

At each occurrence, $R^1$, $R^2$, $R^3$, $R^4$, $R^5$, and $R^6$ are each independently chosen from —H, halide, an organic group, and a hydrophilic group. The method includes precipitating the catalyst. The method includes removing the precipitated catalyst from solution, to provide a purified catalyst.

In various embodiments, the present invention provides a method of purifying a catalyst. The method include contacting a catalyst composition with acid, the catalyst composition including a catalyst, to provide an acidified catalyst composition having a pH of about 0 to about 1 with the catalyst dissolved therein, the catalyst having the structure:

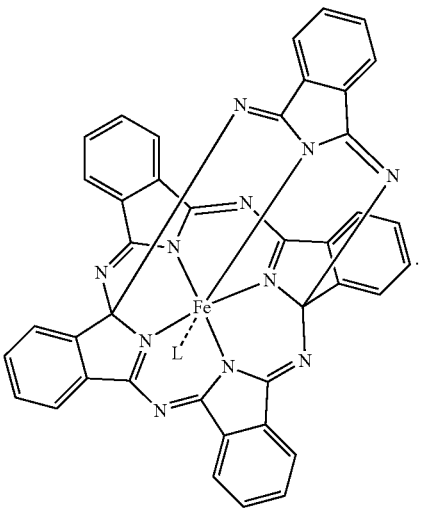

Axial ligand L is $H_2O$. The catalyst composition further includes a secondary catalyst having the structure:

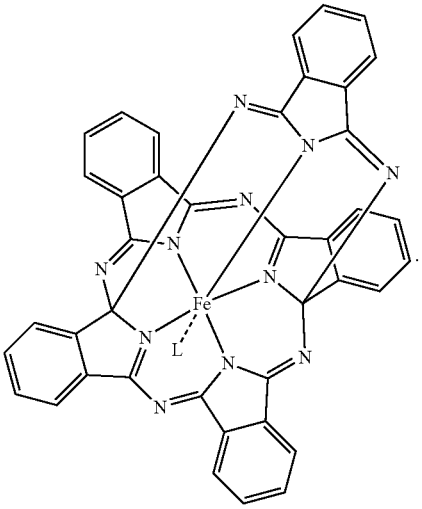

The variable L in the secondary catalyst is MeOH. The method includes precipitating the catalyst, including bringing the pH of the acidified composition to about 1 to about 4. The method includes removing the precipitated catalyst from solution. The method includes washing the precipitated catalyst with water. The method also includes recrystallizing the precipitated catalyst, to provide a purified catalyst.

In various embodiments, the present invention provides a purified catalyst having the structure:

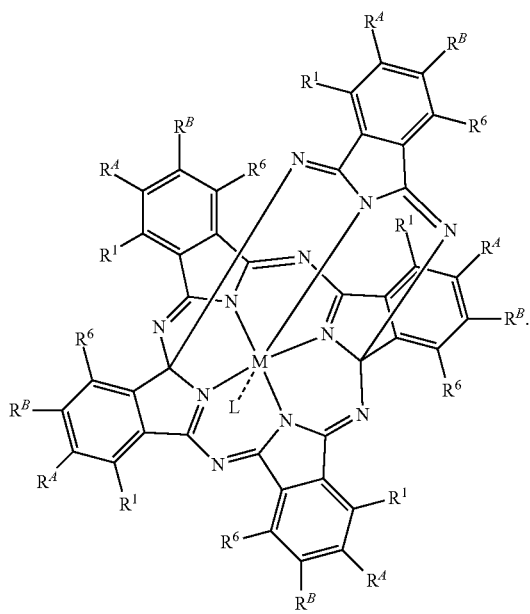

The variable M is a metal. Axial ligand L is a solvent molecule. At each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

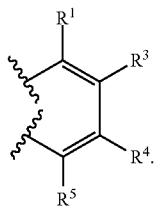

At each occurrence, $R^1$, $R^2$, $R^3$, $R^4$, $R^5$, and $R^6$ are each independently chosen from —H, halide, an organic group, and a hydrophilic group. The purified catalyst is about 95 wt % pure to about 100 wt % pure. In various embodiments, the present invention provides a method of oxidation including contacting an oxidizable starting material with the purified catalyst and an oxidant, to provide an oxidized product.

In various embodiments, the present invention provides a purified catalyst having the structure:

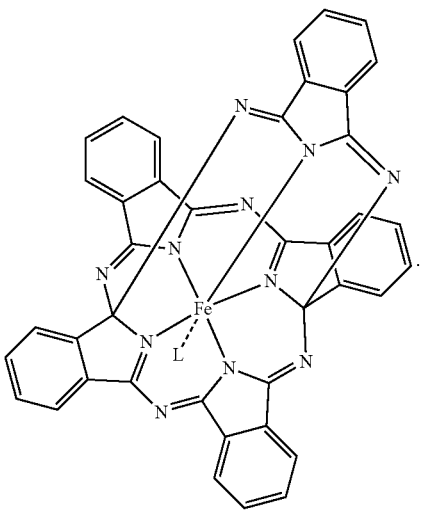

Axial ligand L is $H_2O$. The purified catalyst is about 95 wt % pure to about 100 wt % pure.

In various embodiments, the present invention provides a catalyst having the structure:

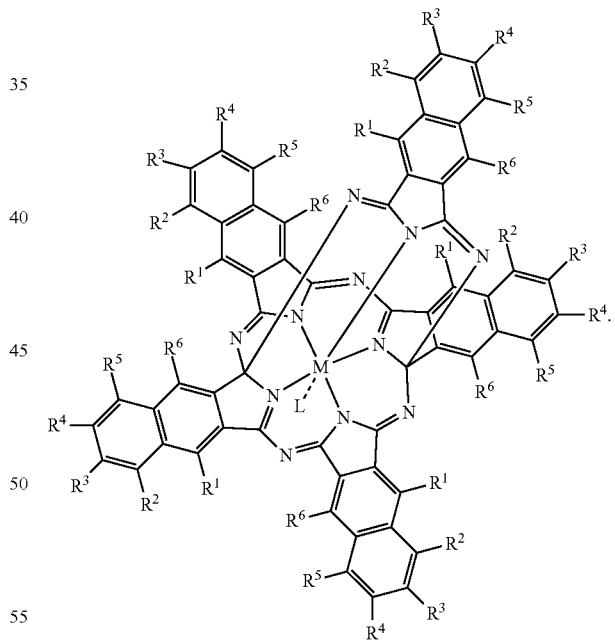

The variable M is a metal. The variable L is a solvent molecule. At each occurrence, $R^1$, $R^2$, $R^3$, $R^4$, $R^5$, and $R^6$ are independently chosen from —H, halide, an organic group, and a hydrophilic group. In various embodiments, the present invention provides a method of oxidation including contacting an oxidizable starting material with the catalyst and an oxidant, to provide an oxidized product.

In various embodiments, the present invention provides a catalyst having the

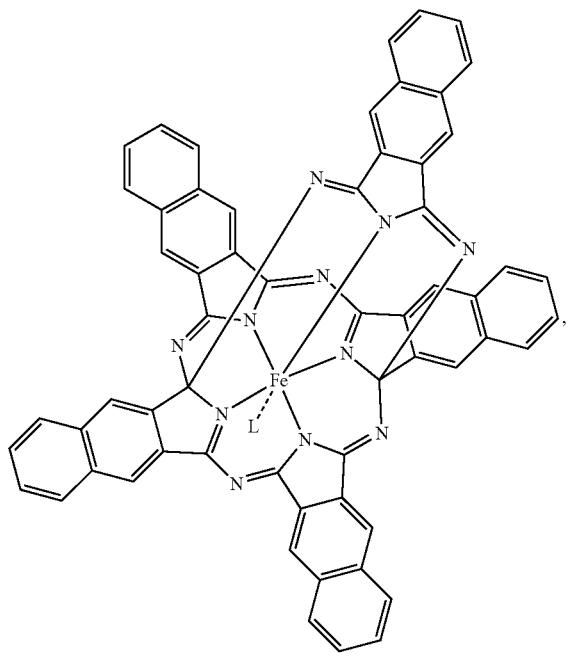

The variable L is H₂O.

In various embodiments, the present invention provides a catalyst having the structure:

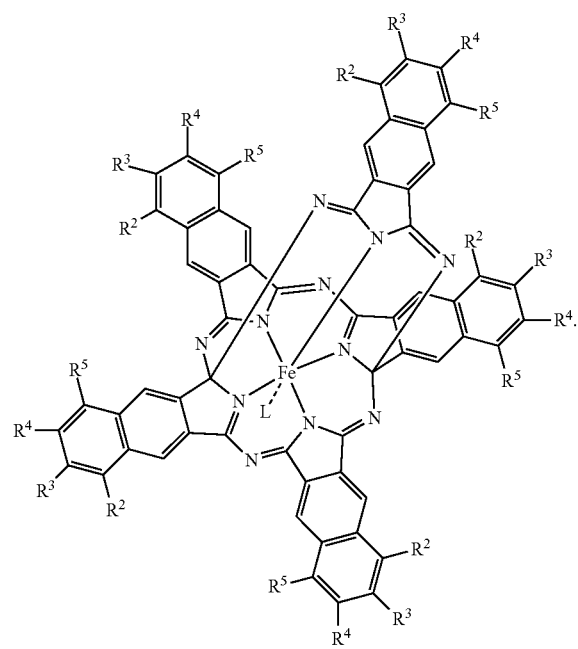

The variable L is water. At each occurrence $R^2$, $R^3$, $R^4$, and $R^5$ are independently chosen from —H and —S(O)(O)OH. At one or more occurrences at least one of $R^2$, $R^3$, $R^4$, and $R^5$ is —S(O)(O)OH (e.g., at least one $R^2$, $R^3$, $R^4$, and $R^5$ in the molecule can be —S(O)(O)OH). In various embodiments, the catalyst can include about five —S(O)(O)OH) groups, located in the positions of $R^2$, $R^3$, $R^4$, $R^5$, or a combination thereof, on one or more of the fused naphthalene units. In various embodiments, the sulfonated form of the catalyst can efficiently catalyze the oxidation of phenol (e.g., carbolic acid) by hydrogen peroxide in an aqueous solution to p-benzoquinone with excellent selectivity for the benzoquinone product, which could be useful for wastewater treatment.

Various embodiments of the method of purifying the catalyst, the purified catalyst, the (L)(18,36-[1,3-diiminobenzo[f]isoindole]phthalocyaninato)M catalyst, derivatives thereof, and methods of using the catalysts and derivatives, can have certain advantages over other purification methods, catalysts, and methods of using the same, at least some of which are unexpected. For example, in some embodiments, the method of catalyst purification can provide purified catalysts that were previously unavailable in a purified state. In some embodiments, the method of catalyst purification can provide purified catalyst more quickly, more easily, and with less expense, than other methods of purifying catalyst.

In various embodiments, the purified catalyst, such as a purified catalyst provided by the method of catalyst purification, can have different properties than less pure forms of the purified catalyst, such as providing catalysis of different types of reactions or providing different rates of catalysis, or such as having different solubility in various solvents. In various embodiments, the purified catalyst can have different solubilities in various solvents, as compared to less pure forms of the purified catalyst, providing the ability to use the purified catalyst in reactions wherein less pure forms of the catalyst would be less effective or ineffective. In various embodiments, the purified catalyst can have greater solubility in non-aromatic alcohols, allowing for the use of the catalyst in a solvent-free oxidation of non-aromatic alcohols, wherein a less pure form of the purified catalyst is less effective or ineffective for solvent-free oxidation of non-aromatic alcohols.

In various embodiments, the (L)(18,36-[1,3-diiminobenzo[f]isoindole]phthalocyaninato)M catalyst can provide different properties than other catalysts, such as catalysis of different types of reactions or different rates of catalysis, or such as having different solubilities in various solvents. In various embodiments, the (L)(18,36-[1,3-diimino-benzo[f]isoindole]phthalocyaninato)M catalyst can provide a more effective scaffold for derivitization than other materials, such as compared to L(14,28-[1,3-diiminoisoindolinato]phthalocyaninato)M catalysts. For example, in various embodiments, while the aromatic rings of an L(14,28-[1,3-diiminoisoindolinato]phthalocyaninato)M catalyst are closer to nitrogen atoms and thus are relatively deactivated toward electrophilic aromatic substitution, the (L)(18,36-[1,3-diimino-benzo[f]isoindole]phthalocyaninato)M catalyst includes aromatic rings that are further spaced from the nitrogen atoms of the bridged phthalocyanine structure, providing greater reactivity toward electrophilic aromatic substitution.

In various embodiments, derivatives of the (L)(18,36-[1,3-diimino-benzo[f]isoindole]phthalocyaninato)M catalyst can provide different properties than other catalysts, such as different catalytic activities than other catalysts, such as catalysis of different types of reactions or different rates of catalysis, or such as having different solubilities in various solvents. In various embodiments, derivatives of the (L)(18,36-[1,3-diimino-benzo[f]isoindole]phthalocyaninato)M catalyst having relatively polar groups substituted thereon, such as sulfonated derivatives, can have enhanced water solubility compared to corresponding catalysts not having such groups substituted thereon, broadening the types of materials that can be used with the catalyst. In various embodiments, derivatives of the (L)(18,36-[1,3-diimino-benzo[f]isoindole]phthalocyaninato)M catalyst having relatively polar groups substituted thereon, such as sulfonated derivatives, can be immobilized onto various substrates, such as ion-exchange resins, providing a heterogeneous catalyst that can operate better than other catalysts in various solvents and that can easily be separated from the reaction after use.

BRIEF DESCRIPTION OF THE FIGURES

The drawings illustrate generally, by way of example, but not by way of limitation, various embodiments discussed in the present document.

FIGS. 4A-M illustrate X-ray data for $(H_2O)(14,28$-[1,3-diiminoisoindolinato]phthalocyaninato)Fe(III) in Tables 2-9, in accordance with various embodiments.

FIGS. 5A-D illustrate mass spectrometry data for $(H_2O)(14,28$-[1,3-diiminoisoindolinato]phthalocyaninato)Fe(III), in accordance with various embodiments.

DETAILED DESCRIPTION OF THE INVENTION

Figure 1A:
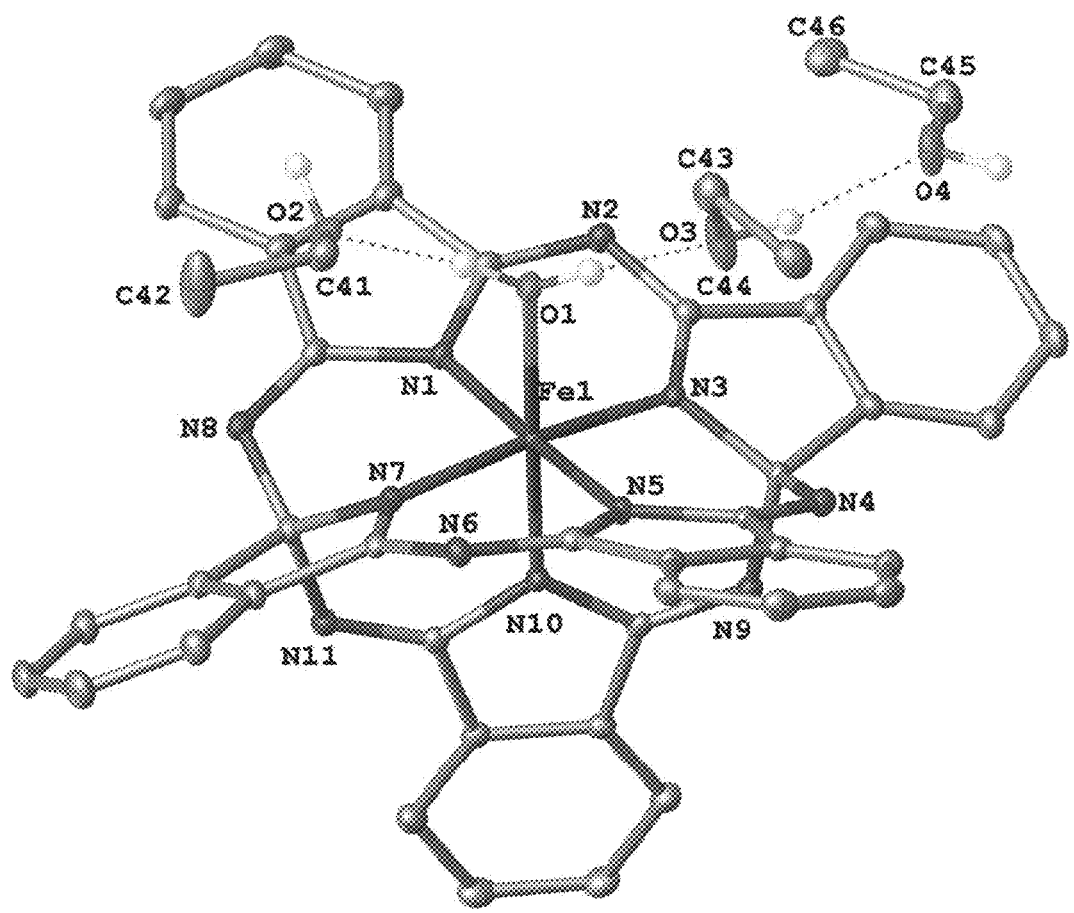
FIGS. 1A-B illustrate molecular drawings generated from X-ray diffraction data for $(H_2O)(14,28$-[1,3-diiminoisoindolinato]phthalocyaninato)Fe(III), in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)

CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "heterocyclyl" as used herein refers to aromatic and non-aromatic ring compounds containing three or more ring members, of which one or more is a heteroatom such as, but not limited to, N, O, and S.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as (C$_a$-C$_b$)hydrocarbyl, wherein a and b are integers and mean having any of a to b number of carbon atoms. For example, (C$_1$-C$_4$)hydrocarbyl means the hydrocarbyl group can be methyl (C$_1$), ethyl (C$_2$), propyl (C$_3$), or butyl (C$_4$), and (C$_0$-C$_b$)hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "room temperature" as used herein refers to a temperature of about 15° C. to 28° C.

The term "standard temperature and pressure" as used herein refers to 20° C. and 101 kPa.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $Al^{3+}$ or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

Method of Purifying a Catalyst.

In various embodiments, the present invention provides a method of purifying a catalyst. The method can include contacting a catalyst composition with acid. The catalyst composition includes a catalyst. The contacting provides an acidified catalyst composition with the catalyst dissolved therein. The method can include precipitating the catalyst. The method can include removing the precipitated catalyst from solution, to provide a purified catalyst.

The acid can be any suitable acid. The acid can include one acid or multiple acids. The acid can include an organic acid or a mineral acid. The acid can include sulfuric acid or hydrochloric acid. The contacting of the catalyst composition with the acid can be sufficient to provide any suitable pH in the acidified solution, such as a pH of about −3 to about 6, about 0 to about 1, or about −3 or less, or about −2, −1, 0, 1, 1.5, 2, 2.5, 3, 3.5, 4, 4.5, 5, or about 6 or more.

The catalyst can be fully dissolved in the acidified catalyst composition. All materials in the acidified catalyst composition can be fully dissolved. If undissolved materials remain in the acidified catalyst composition, the undissolved materials can be removed prior to the precipitation of the catalyst therefrom.

The precipitating of the catalyst from the acidified catalyst composition can include at least partially neutralizing the acidified composition. The at least partially neutralizing includes bringing the acidified composition to any suitable pH, such as a pH of about 0.5 to about 6, about 1 to about 4, or about 0.5 or less, or about 1, 1.5, 2, 2.5, 3, 3.5, 4, 5, or about 6 or more. The at least partially neutralizing can be carried out in any suitable fashion, such as by contacting the acidified composition with a base. The base can be any one or more suitable bases. In some examples, the base can include NaOH or KOH.

The precipitating can include diluting the acidified composition with water. In some embodiments, the diluting can occur prior to the at least partial neutralization. In some embodiments, the diluting can occur after the at least partial neutralization. The diluting can include diluting with any suitable quantity of water such that a convenient volume of formed for removal of the formed precipitate, such as with about 0.01 to about 100 times the volume of the acidified composition, about 2 to about 10 times, or about 0.01 times or less, or about 0.1, 1, 2, 3, 4, 5, 6, 7, 8, 9, 10, 12, 14, 16, 18, 20, 25, 30, 35, 40, 45, 50, 60, 70, 80, 90, or about 100 time the volume of the acidified composition or more.

The removing of the precipitate from solution (e.g., from the acidified solution, which can be at least partially neutralized and diluted) can include washing the precipitated catalyst with water to remove any remaining parts of the acidified composition thereon.

The method can include recrystallizing the precipitated catalyst from a suitable medium, such as from one or more organic solvents. In some embodiments, the method includes recrystallizing the precipitated catalyst from an alcohol, such as methanol, ethanol, or isopropanol.

The purified catalyst can have any suitable purity, such as about 50 wt % pure to about 100 wt % pure, about 95 wt % pure to about 100 wt % pure, greater than 98 wt % pure, about 50 wt % pure or less, or equal to or greater than about 55 wt % pure, 60, 65, 70, 75, 80, 85, 86, 87, 88, 89, 90, 91, 92, 93, 94, 95, 95.5, 96, 96.5, 97, 97.5, 98, 98.5, 99, 99.2, 99.4, 99.6, 99.8, 99.9, 99.99, or about 99.999 wt % pure or more.

The catalyst can have the structure:

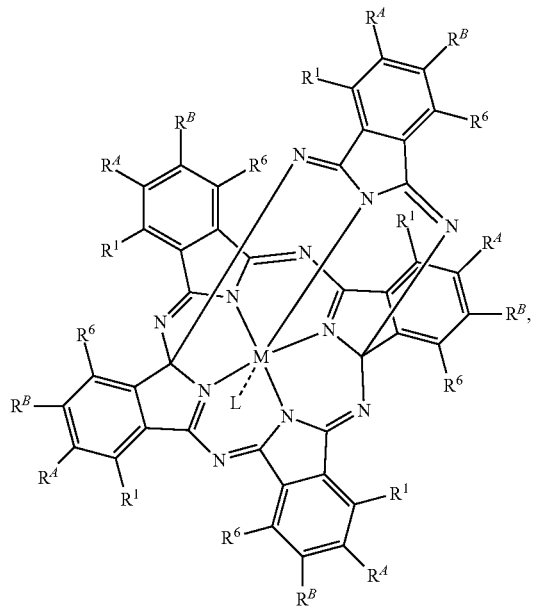

The variable M can be a metal. Herein metal atoms complexed with bridged phthalocyanine- and napththalocyanine structures are drawn showing no valence state. However, the metal atoms have the appropriate valence state that is consistent with the structure shown (e.g., II, III, IV, V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and $H_2O$. The axial ligand L can be $H_2O$.

At each occurrence, $R^A$ and $R^B$ can be independently chosen from —H, halide, an organic group, and a hydrophilic group, or $R^A$ and $R^B$ can together form a fused aromatic ring with the ring upon which $R^A$ and $R^B$ are substituted, $R^A$ and $R^B$ together having the structure:

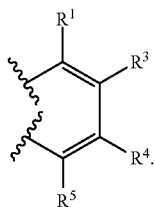

At each occurrence, $R^1$, $R^2$, $R^3$, $R^4$, $R^5$, and $R^6$ can be each independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted $(C_1$-$C_{50})$hydrocarbyl ester thereof, and a combination thereof. The hydrophilic group can be —S(O)(O)OH.

In some embodiments, $R^A$ and $R^B$ can have the structure:

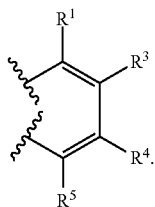

The variables $R^1$, $R^2$, $R^3$, $R^4$, $R^5$, and $R^6$ can be —H.

In some embodiments, $R^A$ and $R^B$ can have the structure:

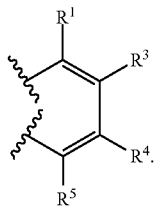

The variables $R^1$ and $R^6$ can be —H. At each occurrence, $R^2$, $R^3$, $R^4$, and $R^5$ can be independently chosen from —H and a hydrophilic group. At one more occurrences at least one of $R^2$, $R^3$, $R^4$, and $R^5$ can be a hydrophilic group.

In some embodiments, $R^A$ and $R^B$ can have the structure:

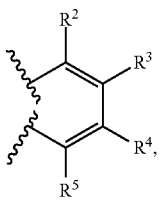

The variables $R^1$ and $R^6$ can be —H. At each occurrence, $R^2$, $R^3$, $R^4$, and $R^5$ can be independently chosen from —H and —S(O)(O)OH. At one more occurrences at least one of $R^2$, $R^3$, $R^4$, and $R^5$ can be —S(O)(O)OH.

In some embodiments, $R^1$, $R^A$, $R^B$, and $R^6$ are —H. The catalyst can have the structure:

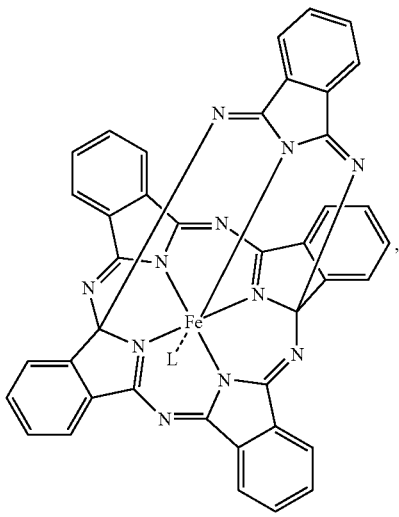

wherein axial ligand L can be $H_2O$.

Any suitable proportion of the catalyst composition can be the catalyst. For example, about 0.001 wt % to about 99.999 wt % of the catalyst composition can be the catalyst, or about 0.001 wt % or less, or equal to or less than about 0.01 wt %, 0.1, 1, 2, 3, 4, 5, 6, 8, 10, 15, 20, 25, 30, 35, 40, 45, 50, 55, 60, 65, 70, 75, 80, 85, 86, 88, 90, 91, 92, 93, 94, 95, 96, 97, 98, 99, 99.9, 99.99, or about 99.999 wt % can be catalyst.

The catalyst composition can further include a secondary catalyst having a different structure than the catalyst. The secondary catalyst can have the structure:

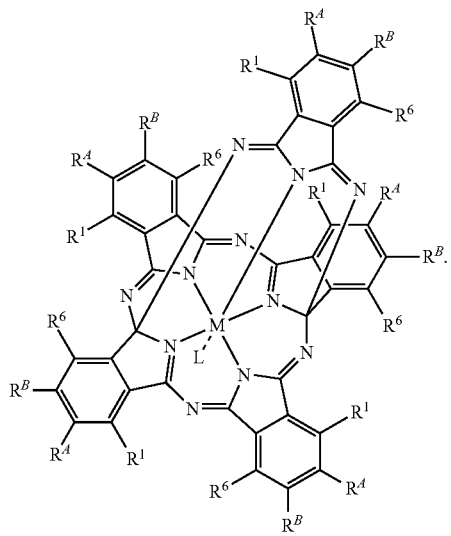

The variables M, L, $R^A$, $R^B$, $R^1$, $R^2$, $R^3$, $R^4$, $R^5$, and $R^6$ can correspond to any atom or group describes for the corresponding variables in the catalyst, so long as the secondary catalyst and the catalyst have different structure.

In various embodiment, the method is particularly valuable for separating a catalyst from a secondary catalyst wherein the catalyst and secondary catalyst have similar or the same structures with the exception of the identity of the axial ligand, L. For example, the method can be particularly valuable for separating a catalyst having an axial ligand L of $H_2O$ from a secondary catalyst having an axial ligand L of MeOH. Thus, for example, the secondary catalyst can have the structure

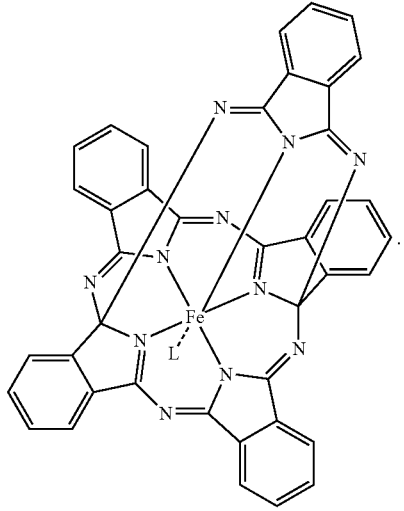

Axial ligand L in the secondary catalyst is MeOH.

The catalyst composition can include any suitable materials in addition to the catalyst, so long as the method can be performed as described herein. In various embodiments, the majority of the catalyst composition can be the catalyst and the secondary catalyst. For example, about 50 wt % to 100 wt % of the catalyst composition can be the catalyst and the secondary catalyst, or about 50 wt % or less, or greater than or equal to about 55 wt %, 60, 65, 70, 75, 80, 85, 86, 88, 90, 91, 92, 93, 94, 95, 96, 97, 98, 99, 99.9, 99.99, 99.999, or about 100 wt %. The purified catalyst can be substantially free of the secondary catalyst (e.g., can include 0 wt %, or less than about 0.0001 wt %, 0.001, 0.01, 0.1, 1, 2, 3, 4, 5, 10, 15, or less than about 20 wt %).

Purified Catalyst.

In various embodiments, the present invention provides a purified catalyst. The catalyst can be purified by any suitable means. In some embodiments, the catalyst is purified via an embodiment of the method of purifying a catalyst described herein. In some embodiments, the purified catalyst can exhibit certain properties not shown by the catalyst under impure conditions. For example, in some embodiments, the purified catalyst can have exhibit different solubilities in various solvents, as compared to the catalyst in impure conditions. The purified catalyst can have any suitable purity, such as about 80 wt %-about 100 wt % pure, about 95 wt % to about 100 wt % pure, about 98 wt % to about 100 wt % pure, or about 80 wt % pure or less, or equal to or greater than about 81 wt %, 82, 83, 84, 85, 86, 87, 88, 89, 90, 91, 92, 93, 94, 95, 96, 97, 98, 99, 99.9, 99.99, or about 99.999 wt % pure or more.

The catalyst can have the structure:

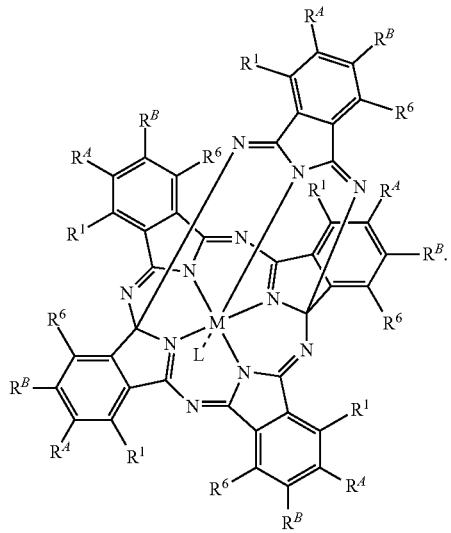

The variable M can be a metal. Herein metal atoms complexed with bridged phthalocyanine- and napththalocyanine structures are drawn showing no valence state. However, the metal atoms have the appropriate valence state that is consistent with the structure shown (e.g., II, III, IV, V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and $H_2O$. The axial ligand L can be $H_2O$.

At each occurrence, $R^A$ and $R^B$ can be independently chosen from —H, halide, an organic group, and a hydrophilic group, or $R^A$ and $R^B$ can together form a fused aromatic ring with the ring upon which $R^A$ and $R^B$ are substituted, $R^A$ and $R^B$ together having the structure:

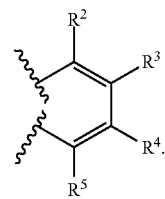

At each occurrence, $R^1$, $R^2$, $R^3$, $R^4$, $R^5$, and $R^6$ can be each independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted ($C_1$-$C_{50}$)hydrocarbyl ester thereof, and a combination thereof. The hydrophilic group can be —S(O)(O)OH.

In some embodiments, $R^A$ and $R^B$ can have the structure:

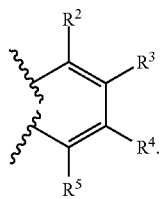

The variables $R^1$, $R^2$, $R^3$, $R^4$, $R^5$, and $R^6$ can be —H.

In some embodiments, $R^A$ and $R^B$ can have the structure:

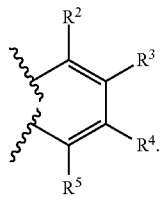

The variables $R^1$ and $R^6$ can be —H. At each occurrence, $R^2$, $R^3$, $R^4$, and $R^5$ can be independently chosen from —H and a hydrophilic group. At one more occurrences at least one of $R^2$, $R^3$, $R^4$, and $R^5$ can be a hydrophilic group.

In some embodiments, $R^A$ and $R^B$ can have the structure:

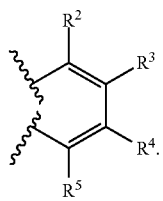

The variables $R^1$ and $R^6$ can be —H. At each occurrence, $R^2$, $R^3$, $R^4$, and $R^5$ can be independently chosen from —H and —S(O)(O)OH. At one more occurrences at least one of $R^2$, $R^3$, $R^4$, and $R^5$ can be —S(O)(O)OH.

In some embodiments, $R^1$, $R^A$, $R^B$, and $R^6$ are —H. The catalyst can have the structure:

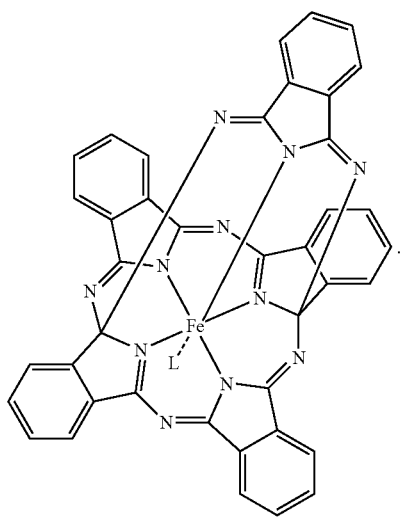

Axial ligand L can be $H_2O$.

Method of Oxidation.

In various embodiments, the present invention provides a method of oxidation. The method can include contacting an oxidizable starting material with any embodiment of a catalyst described herein and an oxidant. The contacting of the oxidizable starting material, the catalyst, and the oxidant, provides an oxidized product. In some embodiments, the catalyst is an embodiment of the purified catalyst described herein.

In various embodiments, the contacting to provide an oxidized product is carried out under solvent-free conditions. Under such solvent-free conditions, the liquid reagents (e.g., the oxidizable starting material and the oxidized product) are suitable for dissolving the catalyst and the oxidizing agent. For example, in various embodiments, the catalyst (e.g., the purified catalyst) is soluble in non-aromatic alcohols, such that oxidation of such non-aromatic alcohols can be carried out without the addition of any other solvents. In some embodiments, the catalyst remains undissolved and operates catalytically from a heterogeneous solution.

The oxidant can be any suitable oxidant. The oxidant can be chosen from tert-butylhydroperoxide, hydrogen peroxide, and combinations thereof.

The oxidizable starting material can be any suitable oxidizable starting material. The oxidizable starting material can be a substituted or unsubstituted $(C_1-C_{50})$hydrocarbyl alcohol. The oxidizable starting material can be chosen from 2-pentanol, 1-pentanol, and 2,4-dimethyl-3-pentanol.

During the contacting to provide the oxidized product, the catalyst can have any suitable turnover number (e.g., the moles of product produced divided by the moles of catalyst used). For example, the turnover number can be about 200 to about 10,000, about 300 to about 1,000, or about 200 or less, or about 250, 300, 350, 400, 450, 500, 550, 600, 650, 700, 750, 800, 850, 900, 950, 1,000, 1,100, 1,200, 1,300, 1,400, 1,500, 1,600, 1,800, 2,000, 2,500, 3,000, 4,000, 5,000, 6,000, 8,000, or about 10,000 or more. During the contacting to provide the oxidized product, the catalyst can have any suitable turnover frequency (e.g., turnover number divided by reaction time). For example, the turnover frequency can be about 500 $h^{-1}$ to about 20,000 $h^{-1}$, about 1,000 $h^{-1}$ to about 4,000 $h^{-1}$, about 500 $h^{-1}$ or less, or about 600 $h^{-1}$, 800, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 4,000, 4,500, 5,000, 6,000, 7,000, 8,000, 9,000, 10,000, 15,000, or about 20,000 $h^{-1}$ or more.

Catalyst.

In various embodiments, the present invention provides a catalyst. The catalyst can have any suitable purity, such as about 0.001 wt % to 100 wt %, 50 wt % to about 90 wt %, or about 0.001 wt % or less, or equal to or greater than about 0.001 wt %, 0.01, 0.1, 1, 2, 3, 4, 5, 6, 8, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, 99.9, 99.99, or about 99.999 wt % or more.

The catalyst can have the structure:

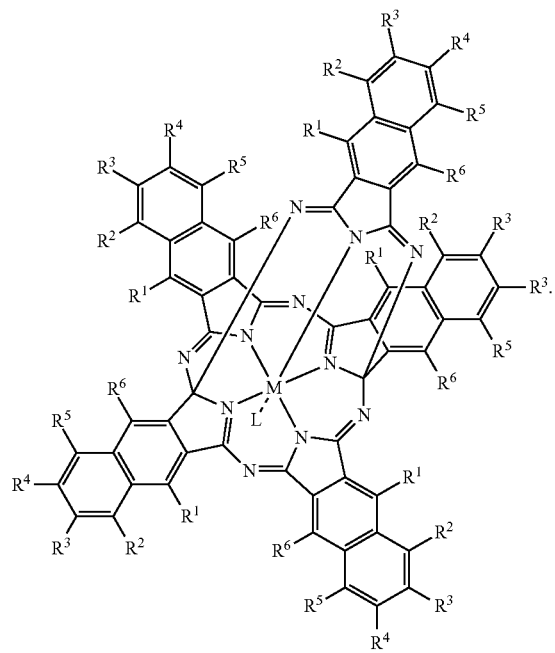

The variable M can be a metal. Herein metal atoms complexed with bridged phthalocyanine- and napththalocyanine structures are drawn showing no valence state. However, the metal atoms have the appropriate valence state that is consistent with the structure shown (e.g., II, III, IV, or V). The variable M can be a Group VIII or IX transition metal. The variable M can be chosen from Co and Fe. The variable M can be Fe (e.g., Fe(III)). The axial ligand L can be a solvent molecule. The axial ligand L can be chosen from MeOH and H$_2$O. The axial ligand L can be H$_2$O.

At each occurrence, R$^1$, R$^2$, R$^3$, R$^4$, R$^5$, and R$^6$ can be independently chosen from —H, halide, an organic group, and a hydrophilic group. The hydrophilic group can be any suitable hydrophilic group. For example, at each occurrence, the hydrophilic group can be chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted (C$_1$-C$_{50}$)hydrocarbyl ester thereof, and a combination thereof. The hydrophilic group can be —S(O)(O)OH.

In some embodiments, R$^1$ and R$^6$ are —H, and at each occurrence, R$^2$, R$^3$, R$^4$, and R$^5$ are independently chosen from —H and a hydrophilic group. At one or more occurrences at least one of R$^2$, R$^3$, R$^4$, and R$^5$ can be a hydrophilic group (e.g., at least one of R$^2$, R$^3$, R$^4$, or R$^5$ in the molecule is a hydrophilic group).

In some embodiments, R$^1$ and R$^6$ are —H, and at each occurrence, R$^2$, R$^3$, R$^4$, and R$^5$ are independently chosen from —H and —S(O)(O)OH. At one or more occurrences at least one of R$^2$, R$^3$, R$^4$, and R$^5$ can be —S(O)(O)OH (e.g., at least one of R$^2$, R$^3$, R$^4$, or R$^5$ in the molecule can be —S(O)(O)OH).

Various embodiments of the present invention provide a method of oxidation including contacting an oxidizable starting material with the catalyst and an oxidant, to provide an oxidized product. The oxidizable starting material can be any suitable oxidizable starting material, such as a substituted or unsubstituted (C$_1$-C$_{50}$)hydrocarbyl alcohol, such as 2-pentanol, 1-pentanol, 2,4-dimethyl-3-pentanol, or isopropanol. The oxidant can be any suitable oxidant, such as tert-butylhydroperoxide, hydrogen peroxide, and combinations thereof. In various embodiments, the contacting to provide an oxidized product can be carried out under solvent-containing or solvent-free conditions (e.g., wherein the reagents act as the solvent).

In various embodiments, the present invention provides a method of forming the catalyst. For example, the method can include combining a suitable M-containing reagent (e.g., Fe(OAc)$_2$) with a suitable material, such as 2,3-naphthalenedicarbonitrile, under conditions sufficient to produce the catalyst.

In various embodiments, the present invention provides a method of forming a derivatized catalyst. The method can include adding a hydrophilic group to the catalyst, such as by electrophilic aromatic substitution. The method can include adding to the catalyst one or more of —C(O)OH, —O—C(O)OH, —P(O)(OH)$_2$, —OP(O)(OH)$_2$, —S(O)(O)OH, —OS(O)(O)OH, a salt thereof, and a substituted or unsubstituted (C$_1$-C$_{50}$)hydrocarbyl ester thereof. The method can include adding to the catalyst —S(O)(O)OH, such as via treatment with sulfuric acid.

In various embodiments, the derivatized catalyst can have a greater water solubility than the un-derivatized catalyst, due to the added one or more hydrophilic groups. Various embodiments of the present invention provide a method of oxidation including contacting a suitable oxidizable starting material, a suitable oxidant, the derivatized catalyst, and water

EXAMPLES

Various embodiments of the present invention can be better understood by reference to the following Examples which are offered by way of illustration. The present invention is not limited to the Examples given herein.

Part I. (14,28-[1,3-diiminoisoindolinato]phthalocyaninato)Fe(III)

Example 1.1

Synthesis of (H$_2$O/MeOH)(14,28-[1,3-diiminoisoindolinato]phthalocyaninato)Fe(III) (1)

Iron(II) acetate tetrahydrate (44.2 mg, 0.254 mmol), 1,2-dicyanobenzene (194.6 mg, 1.52 mmol) and 4.0 mL methanol were combined in a glass vial, which was then placed in a PTFE-lined stainless steel autoclave and heated for seven days at 130° C. Upon opening the autoclave, a dark brown solution was observed, along with some dark red crystals, suitable for X-ray crystallography, and apparently amorphous solids. The solution was allowed to evaporate and the residue was dissolved in a minimal amount of dichloromethane. This solution was loaded onto a silica gel flash column. A red-brown band remained strongly adsorbed at the top of the column as organic impurities were eluted with 100 mL of a 50% toluene: 50% dichloromethane mixture, followed by 1.0 L of 100% toluene, then 100 mL of a 50% toluene: 50% dichloromethane mixture, then 200 mL of 100% dichloromethane. A broad red-brown band then quickly desorbed and eluted with 100% methanol and was collected. Slow evaporation of the solvent yielded dark red crystals of 1 (46.0 mg, 0.0558-0.0570 mmol, 22.0-22.5%) based upon the starting iron reagent. Because 1 was obtained with varying proportions of methanol and water as axial ligand L, the yield is reported as a range between 22.0% (assuming L is 100% water, with three additional non-ligand molecules of methanol present in the crystal lattice) and 22.5% (assuming L is 100% methanol, with two additional non-ligand molecules of methanol present in the crystal lattice). The relationship between the identity of L and the number of co-crystallized methanol molecules is inferred from crystallographic results. The identity of this sample was confirmed by comparison of its IR and UV-VIS spectra to those of an authentic sample from a similar reaction that was fully characterized via X-ray crystallography. Satisfactory elemental analysis of 1 could not be obtained due to partial solvent loss from the crystal lattice upon drying. IR $\bar{v}_{max}$/cm$^{-1}$ 3413 br, 3057 w, 2820 w, 1623 m, 1557 s, 1521 s, 1472 s, 1444 s, 1396 s, 1353 w, 1321 m, 1310 m, 1296 m, 1207 m, 1161 m, 1144 m, 1123 s, 1097 m, 1079 m, 1027 s, 1007 m, 993 m, 964 w, 948 m, 923 m, 880 w, 845 w, 803 w, 778 m, 753 m, 730 vs, 701 m, 684 w, 666 w, 651 w, 637 w and 625 w. These data match with those obtained from an authentic sample of 1 characterized by X-ray crystallography. The catalyst 1 was not soluble in water. The catalyst 1 had poor solubility in non-aromatic alcohols (zero to nearly zero solubility).

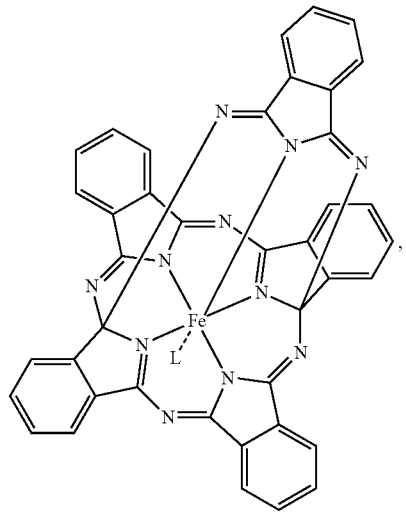

wherein L is H$_2$O or MeOH

Alternatively, up to a 40% yield of pure material was obtained via careful methanol washing of crystals taken directly from the un-chromatographed residue in the reaction vessel.

Example 1.2

Purification of (H$_2$O)(14,28-[1,3-diiminoisoindolinato]phthalocyaninato)Fe(III) (2)

The mixed catalyst 1 from Example 1.1 was provided via careful methanol washing of crystals taken directly from the un-chromatographed residue in the reaction vessel. A mass of 45 mg of the resulting solid was then dissolved in concentrated sulfuric acid (3 mL) and stirred overnight at room temperature. The solution was then diluted to 20 mL with water and the pH was raised to ~2.0 using NaOH. The resulting solid was then collected by filtration and washed with copious water. Pure crystals were obtained by triturating this solid with ethanol followed by crystallization from the ethanol via slow evaporation, to give (H$_2$O)(14,28-[1,3-diiminoisoindolinato]phthalocyaninato)Fe(III) (2).

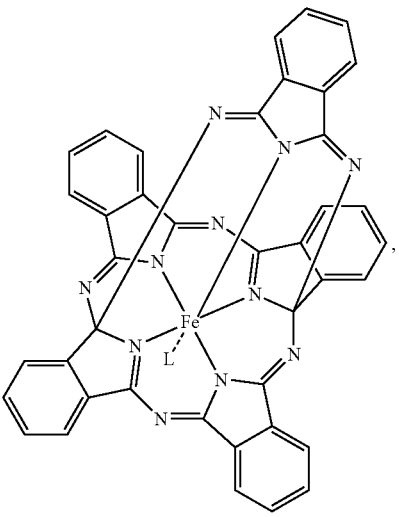

wherein L is H$_2$O

Figure 1B:
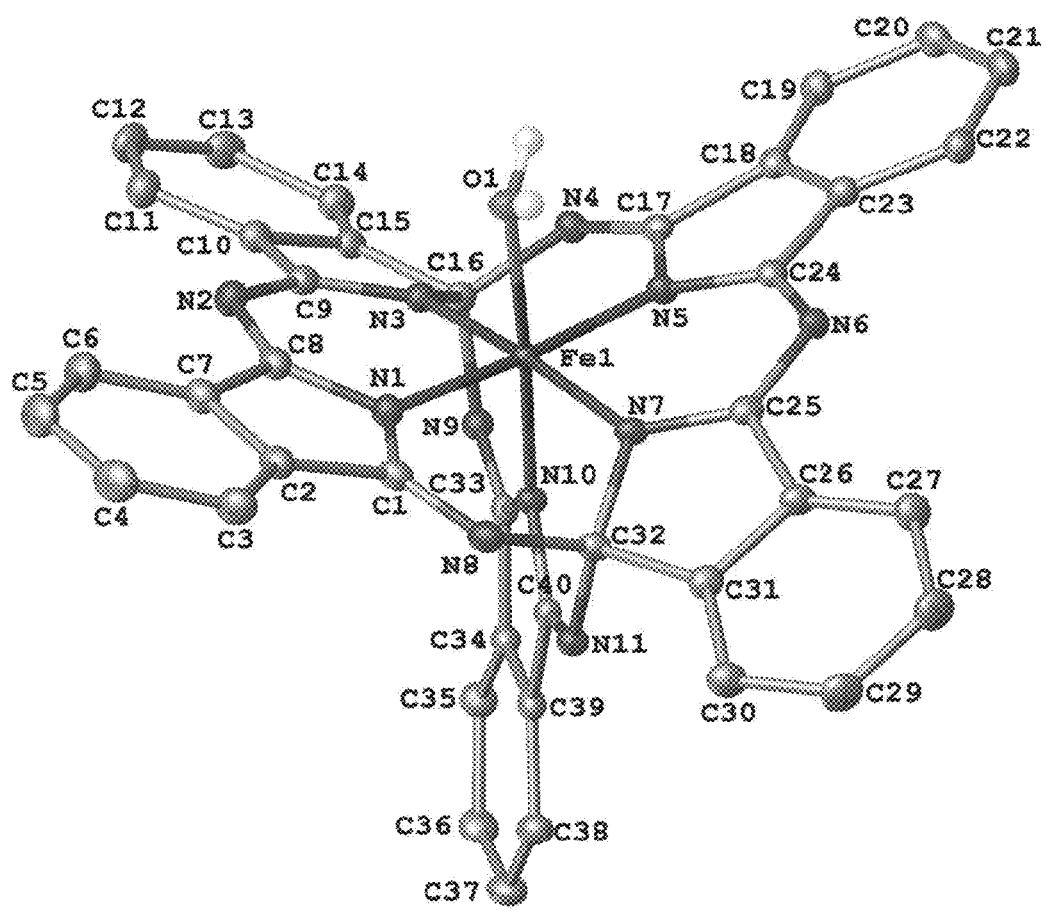

Molecular drawings generated from X-ray diffraction data for 2 are illustrated in FIGS. 1A-B. The molecular drawings are shown with 50% (FIG. 1A) and 60% (FIG. 1B) probability ellipsoids, with H atoms not involved in hydrogen bonding omitted for clarity. Methanol solvate molecules are omitted from FIG. 1B. IR data (KBr) was as follows (cm$^{-1}$) 3241 (br), 1628 (m), 1563 (s), 1519 (s), 1471 (s), 1441 (s), 1398 (m), 1322 (w), 1296 (w), 1193 (w), 1101 (s), 1031 (m), 730 (s), 459 (s). The catalyst 2 was not soluble in water, but had excellent solubility in all alcohols, including non-aromatic alcohols, other than methanol.

Example 1.3

Use of (H$_2$O)(14,28-[1,3-diiminoisoindolinato] phthalocyaninato)Fe(III) (2)

The catalyst 2 from Example 1.2 was used in various reactions. The turnover number (TON) indicates the moles of product produced divided by the moles of catalyst used. All reactions were carried out in 3.0 mL of neat substrate in magnetically stirred round bottom flasks that were loosely closed with rubber septa. Catalysts were dissolved in the substrate, followed by oxidant addition. At the conclusion of the given reaction times, product mixtures were passed through a short plug of silica gel with diethyl ether to remove the catalyst. Reactions employed excess tert-butylhydroperoxide (TBHP) oxidant, added as a 70% by weight solution in water. Products were identified and quantified by GC-MS employing naphthalene as an internal standard.

Example 1.3.1

Oxidation of 2-pentanol to 2-pentanone

In a 30 min. reaction at room temperature, TON=928, corresponding to a catalyst turnover frequency (TOF, =TON divided by reaction time) of 1856 h$^{-1}$. A mass of 2.5 mg (3.1 μmol) of catalyst was employed in this reaction, shown in Scheme 1. The yield on the basis of TBHP oxidant was 33%, determined via gas chromatography-mass spectrometry (GC-MS).

Scheme 1. Oxidation of 2-pentanol to 2-pentanone.

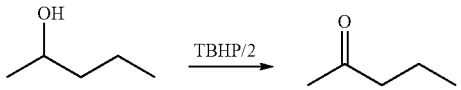

Example 1.3.2

Oxidation of 1-pentanol to pentanal

In a 15 min. reaction at room temperature TON=356, corresponding to TOF=1426 h$^{-1}$. A mass of 1.0 mg (1.2 µmol) of catalyst was employed in this reaction, shown in Scheme 2. The yield on the basis of TBHP oxidant was 5.6%, determined via (GC-MS).

Scheme 2. Oxidation of 1-pentanol to pentanal.

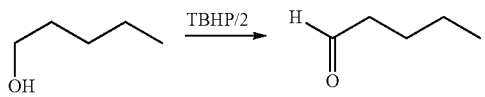

Example 1.3.3

Oxidation of 2,4-dimethyl-3-pentanol to 2,4-dimethyl-3-pentanone

In a 15 min. reaction, TON=750, corresponding to TOF=3000 h$^{-1}$. The reaction temperature was 55° C., necessary to provide adequate mixing/miscibility of the oxidant and substrate. A mass of 1.5 mg (1.9 µmol) of catalyst was employed in this reaction, shown in Scheme 3. The yield on the basis of TBHP oxidant was 12%, determined via (GC-MS).

Scheme 3. Oxidation of 2,4-dimethyl-3-pentanol to 2,4-dimethyl-3-pentanone.

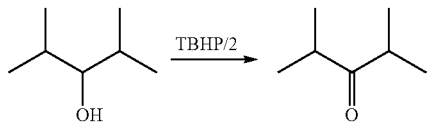

Example 1.3.4

Oxidation of Cyclohexanol to Cyclohexanone

In a 15 min. reaction at room temperature, TON=520, corresponding to TOF=1000 h$^{-1}$. A mass of 1.1 mg (1.4 µmol) of catalyst was employed in this reaction, shown in Scheme 4. The yield on the basis of TBHP oxidant was 8.2%, determined via (GC-MS).

Scheme 4. Oxidation of cyclohexanol to cyclohexanone.

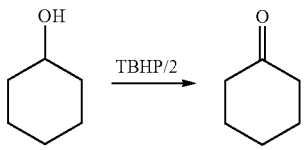

Part II. (18,36-[1,3-diimino-benzo[f]isoindole] phthalocyaninato)Fe(III)

Example 2.1

Synthesis of (H$_2$O)(18,36-[1,3-diimino-benzo[f] isoindole]phthalocyaninato)Fe(III) (3)

Fe(OAc)$_2$ (34.4 mg, 0.1978 mmol) and 2,3-naphthalenedicarbonitrile (212.8 mg, 1.194 mol) were combined in a glass vial with 4.0 mL methanol. The vial was then sealed in a Teflon-lined autoclave and heated for one week at 130° C. Upon opening the autoclave, the vial was observed to contain a dark crystalline solid ((H$_2$O)(18,36-[1,3-diimino-benzo[f]isoindole]phthalocyaninato)Fe(III) (3)) and lightly colored powdery solid impurities and a pale yellow/orange supernatant liquid. Single crystals of the dark solid suitable for X-ray study were obtained from such reactions, having only water as the axial ligand. Although only 5 equivalents of 2,3-naphthalenedicarbonitrile are required to produce 3, it has been found that yields are higher when using 6 equivalents, possibly due to an oligomerization side-reaction of the 2,3-naphthalenedicarbonitrile. The reaction scheme is shown in Scheme 5.

Scheme 5. Synthesis of (H$_2$O)(18,36-[1,3-diimino-benzo[f]isoindole]phthalocyaninato)Fe(III) (3).

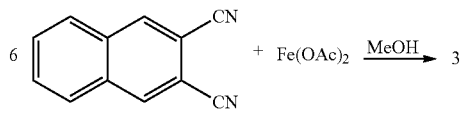

Figure 2A:
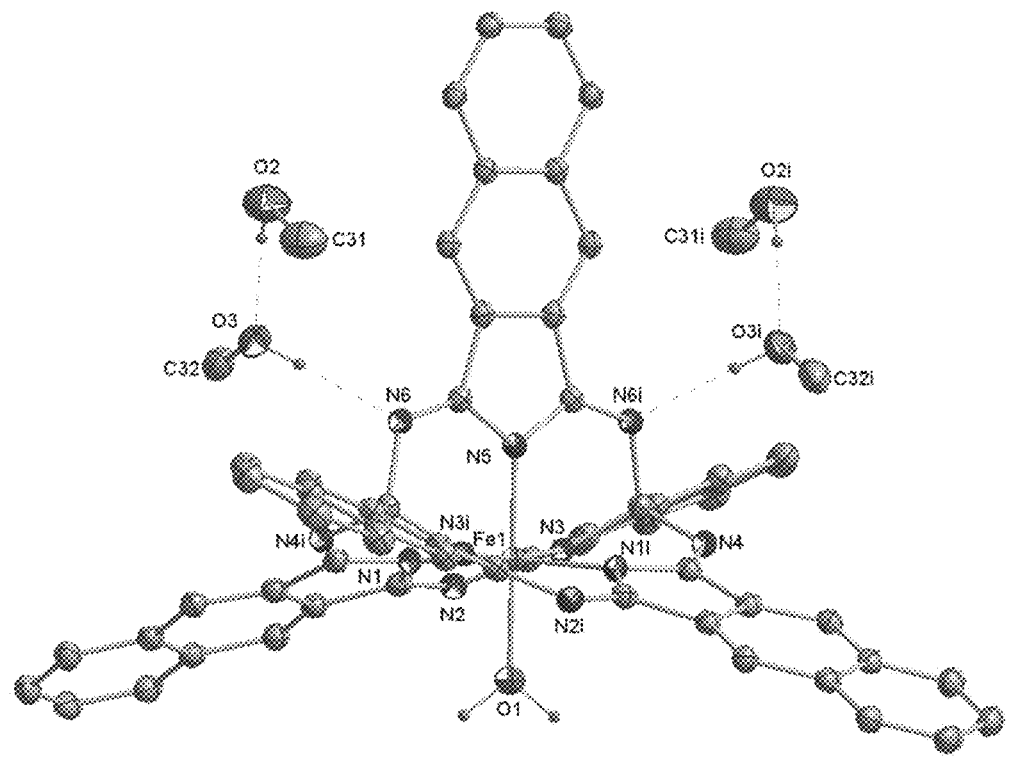
FIGS. 2A-B illustrate molecular drawings generated from X-ray diffraction data for $(H_2O)(14,28$-[1,3-diiminoisoindolinato]phthalocyaninato)Fe(III), in accordance with various embodiments.
Figure 2B:
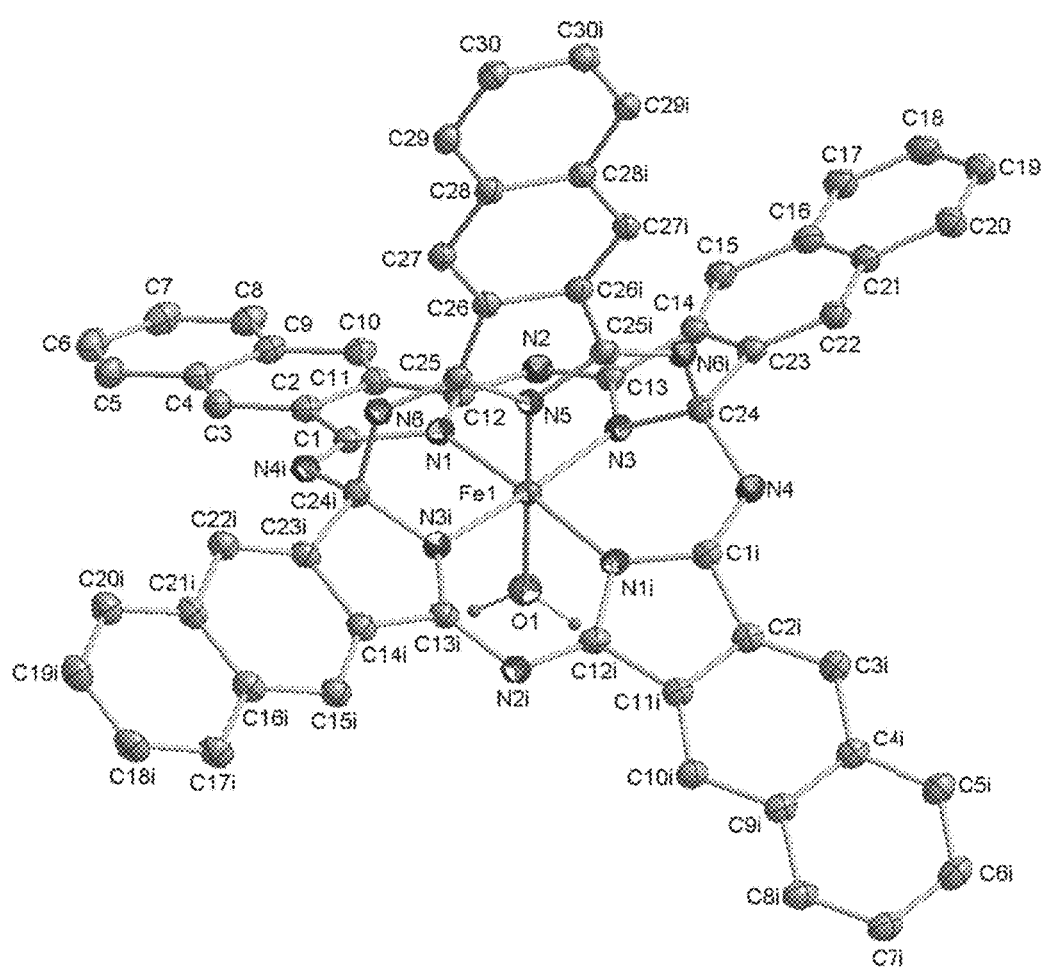

Purification of the bulk product was accomplished by washing with methanol and water, followed by stirring in glacial acetic acid, followed by further water washing. The resulting red crystalline solid was taken up into dichloromethane and loaded onto a silica gel column, whereon it adsorbed very strongly to the top of the column. Copious dichloromethane was eluted through the column to remove impurities (this was essentially a solid phase extraction). The desired compound was then removed from the column by elution of 50% acetone/50% dichloromethane as a dark red band. The product solution thus obtained was evaporated and recrystallized from dichloromethane to produce a dark red solid. Removal of trace solvents under vacuum afforded a material with an IR spectrum (KBr pellet) matching that of an authentic sample that had been characterized via X-ray methods. The IR data was as follows (KBr, cm$^{-1}$): 3055.7 (w), 1622.0 (s), 1561.0 (vs), 1522.0 (s), 1463.0 (vs), 1435.0 (s), 1372.2 (m), 1336.2 (m), 1264.7 (w), 1216.5 (w), 1189.6 (m), 1133.0 (m), 1097.7 (m), 1049.5 (w), 1020.0 (m), 997.8 (m), 968.0 (m), 894.6 (s), 801.5 (w), 787.5 (w), 756.7 (s), 742.5 (s), 569.2 (s), 521.4 (w), 504.6 (w), 473.1 (s). Molecular drawings generated from X-ray diffraction data for 3 are illustrated in FIGS. 2A-B. The molecular drawings are shown with H atoms attached to carbon atoms omitted for clarity. Methanol solvate molecules are omitted from FIG. 2B.

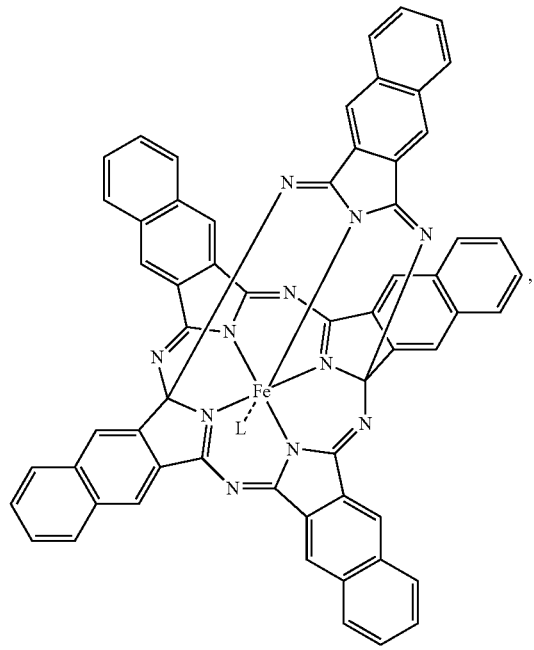

wherein L is $H_2O$

Example 2.2

Sulfonated Derivative (4)

The $(H_2O)(18,36\text{-}[1,3\text{-diimino-benzo}[f]\text{isoindole}]\text{phthalocyaninato})Fe(III)$ (3) from Example 2.1 (85 mg) was treated with fuming sulfuric acid (3.0 mL) at room temperature for 68 hours, then the solution was diluted with water and neutralized with NaOH. The resulting solution was allowed to evaporate to dryness and then extracted with ethanol, producing a reddish brown solution that was filtered to remove the presumed $Na_2SO_4$ byproduct produced during the neutralization step. The filtrate was allowed to evaporate, resulting in a reddish solid with excellent water solubility that is believed to include the sodium salt of the sulfonated iron complex (4) along with sodium sulfate impurities.

Example 2.3

Oxidation of Isopropanol to Acetone

The sulfonated derivative 4 from Example 2.2 was combined with isopropanol and excess hydrogen peroxide in water (30 wt % $H_2O_2$ in water), which formed acetone, identified via reverse phase high pressure liquid chromatography (HPLC). The reaction is shown in Scheme 6.

Scheme 6. Oxidation of isopropanol to acetone.

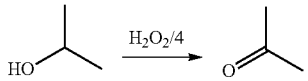

Example 2.4

Immobilization on ion-exchange resin and oxidation of 2-pentanol to 2-pentanone

The sulfonated derivative 4 from Example 2.2 was immobilized on the anion exchange resin diethylaminoethanol (DEAE)-Sepharose® (a beaded-form of agarose extracted from seaweed). The immobilized catalyst was combined with 2-pentanol and TBHP, which formed 2-pentanone, as shown in Scheme 7.

Scheme 7. Immobilaztion on ion-exchange resin and oxidation of 2 pentanol to 2-pentanone.

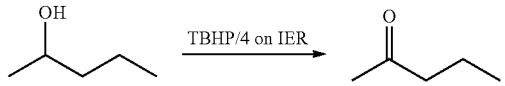

Example 2.5

Characterization of Sulfonated Derivative 4

The sulfonated catalyst(s) 4, which are pentasulfonated derivatives of scaffold complex 3, have been determined to possess the general formula $[C_{60}H_{(30-x)}FeN_{11}O_{15}S_5]^{x-}$, where X represents both the number of deprotonated sulfonic acid groups (thus rendering these groups as sulfonates) and the overall charge on the anionic sulfonate complex. The charge compensating cations are $Na^+$. The characterization has been made by high resolution electrospray ionization (ESI) mass spectrometry (negative ion mode) through comparison of calculated and observed m/z ratios, where m is ion mass and z is absolute ion charge, and also by comparison of observed and calculated isotopic distribution patterns. In all cases, axial water ligands on 4 are lost during ionization. In some cases, observed peaks correspond to sodium ion adducts of the pentasulfonated complexes that form during the ionization process. While not providing direct structural information, the mass spectra clearly show that the starting material has been sulfonated five times. Presumably, there exists one sulfonyl (or sulfonate) group on each outer ring of each complex. Isomers may be present.

Specifically, the following are observed in spectra recorded on sample MEI141 (3279):

(1) A peak is observed at m/z=338.9896, corresponding to a tetraanion of formula $[C_{60}H_{26}FeN_{11}S_5O_{15}]^{4-}$, which is the formula for the pentasulfonated complex, presumably with one sulfonate group on each of the five outermost aromatic rings, after loss of the axial water ligand during ionization and with one of the sulfonate groups existing as a (protonated) sulfonic acid group. The calculated m/z for this tetraanion is 338.9897, within 0.3 ppm of the observed value. Observed and calculated isotopic patterns around this peak match very well. We do not know whether the protonated sulfonic acid group exists in the original solution, or rather if the protonation occurs during the ESI process of a completely deprotonated pentasulfonated complex.

(2) A peak is observed at m/z=344.4850, corresponding to a sodium ion adduct of the pentasulfonated complex with each sulfonic acid group deprotonated and after loss of the axial water ligand, $[C_{60}H_{25}FeN_{11}S_5O_{15}Na]^{4-}$. The calculated m/z for this adduct is 344.4852, within 0.6 ppm of the observed value. Observed and calculated isotopic patterns around this peak match very well. Presumably, the sodium ion adduct formed during the ESI process, due to the highly charged nature of the completely deprotonated pentasulfonated complex and presence of many sodium ions in the analyte solution. By completely deprotonated, we mean that all of the five sulfonic acid groups have been deprotonated.

(3) A peak is observed at m/z=459.6495, corresponding to a sodium ion adduct of the pentasulfonated complex after the axial water ligand is lost and where one of the sulfonate groups exists as a (protonated) sulfonic acid group to give $[C_{60}H_{26}FeN_{11}NaS_5O_{15}]^{3-}$. The calculated m/z for this trianion is 459.6493, within 0.4 ppm of the observed value. Observed and calculated isotopic patterns around this peak match very well. We do not know whether the protonated sulfonic acid group exists in the original solution, or rather if the protonation occurs during the ESI process of a completely deprotonated pentasulfonated complex.

(4) A peak is observed at m/z=466.9765, corresponding to a disodium adduct of the pentasulfonated complex with each sulfonic acid group deprotonated and after loss of the axial water ligand, $[C_{60}H_{25}FeN_{11}Na_2S_5O_{15}]^{3-}$. The calculated m/z for this trianionic adduct is 466.9766, within 0.2 ppm of the observed value. Observed and calculated isotopic patterns around this peak match very well.

Part III. Oxidation of Non-Benzylic Alcohols Catalyzed by a "Helmet" Phthalocyaninato Iron Complex in the Absence of Added Organic Solvent: A Seemingly Minor Structural Modification of a Known Catalyst Vastly Expands Versatility The "helmet" metallophthalocyaninato iron(III) system is a very effective catalyst for the oxidation of unactivated primary and secondary alcohols under solvent free conditions, as shown in Scheme 8.

Scheme 8. Solvent-free oxidation of unactivated primary and secondary alcohols.

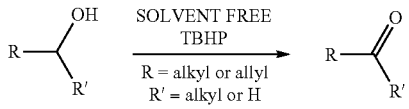

R = alkyl or allyl
R' = alkyl or H

An iron(III) complex bearing a bicyclic pentadentate 14,28-[1,3-diiminoisoindolinato]phthalocyaninato (diiPc) ligand and an axial water ligand is very effective as a catalyst in oxidation reactions of three secondary aliphatic alcohols (2-pentanol, 2,4-dimethyl-3-pentanol and cyclohexanol), one primary aliphatic alcohol (1-pentanol), and one bifunctional allyl alcohol (5-hydroxymethylfurfural) with tert-butylhydroperoxide (TBHP) in the absence of added organic solvent other than the substrates themselves. All reactions proceed with high turnover numbers (TON) and turnover frequency (TOF) relative to related catalytic systems. Selectivity for the expected aldehyde and ketone products is excellent, with no observable over-oxidation to carboxylic acids in the two cases where acids could be expected as possible products. Surprisingly, the presence of only water as the monodentate axial ligand in the catalyst provides solubility in non-aromatic substrates, in sharp contrast to observations for diiPc complexes of Fe(III) where the axial monodentate ligand completing the coordination sphere of iron is a mixture of methanol and water strongly favouring methanol. The formulation of the catalyst employed in reactions described here has been conclusively established via single crystal X-ray methods. The catalysis results presented represent a significant extension and generalization of utility for the (diiPc)Fe(III) system in solvent-free alcohol oxidations, because four of the five substrates investigated can be described as unactivated alcohols, contrasting with previous studies on this general catalytic system that involved only activated (benzylic) alcohols.

In the present Part is described the catalytic oxidation of five non-benzylic alcohol substrates with tert-butylhydroperoxide (TBHP), employing a diiPc complex of iron(III) that shows markedly increased solubility in non-aromatic alcohols relative to that observed for the specific complexes used as catalysts in Parts I and II. The solubility of the catalyst employed in the work described in the present paper is surprising following its characterization via X-ray crystallography, given the fact that it results from a seemingly minor modification of the complex. Because of this enhanced solubility, the helmet metallophthalocyaninato iron(III) system exhibits catalytic behavior with a much wider and more diverse range of substrates.

The oxidation of primary and secondary alcohols is a transformation that remains of fundamental importance in organic synthesis. The observation of good catalytic activity for the diiPcFe(III) moiety in the oxidation of unactivated alcohols represents a significant step forward, furthering the potential of the diiPcFe(III) system as a truly green catalyst. The TON and TOF values reported in the present Part compare favorably with those observed for similar alcohol oxidation systems, especially given the solvent-free nature of the transformations.

Equipment and materials. All solvents (HPLC grade or higher) were purchased from commercial sources and used without drying or distillation. All reagents were obtained from commercial sources in the highest available purity and used as received. The FT-IR spectrum was recorded on a Nicolet iS5 spectrometer using a KBr pellet. Products from all oxidation reactions were analyzed via GC-MS using an Agilent 7890A gas chromatograph employing an Agilent HP-5 ms column of dimensions 30 m×0.25 mm and ultra-high purity helium carrier gas, operating in combination with an Agilent 5975C mass spectrometer.

Example 3-1

Catalyst Preparation

Figure 3:
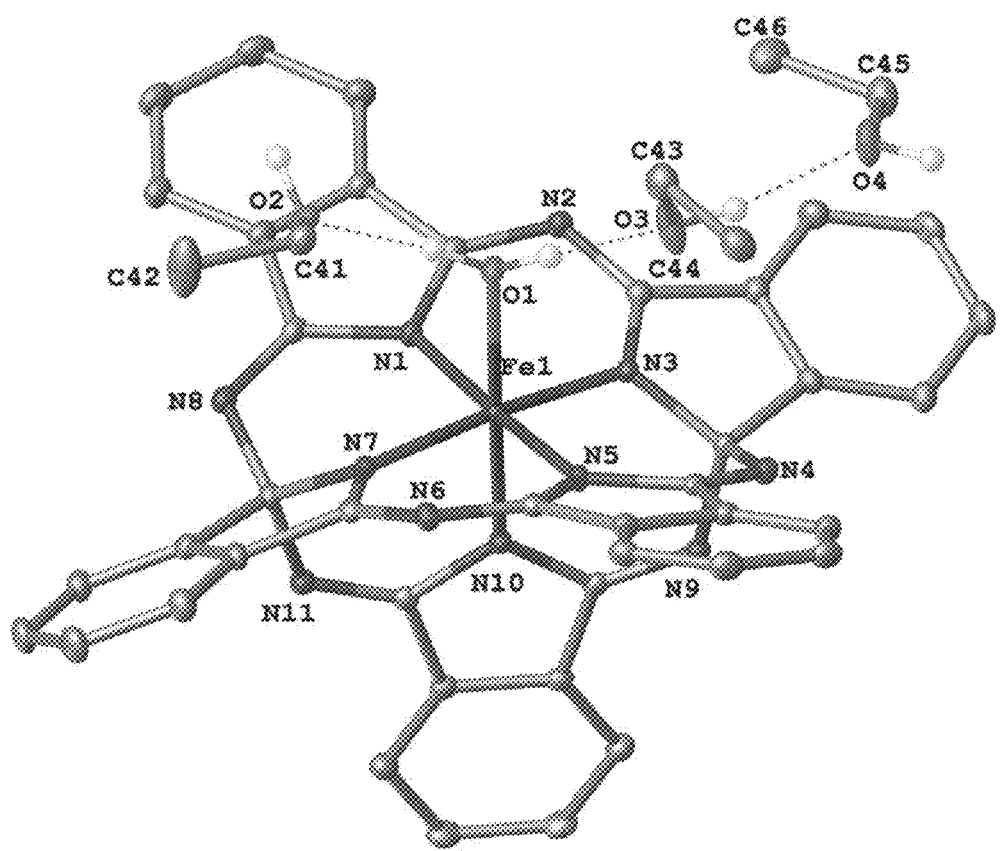
FIG. 3 illustrates a molecular drawing generated from X-ray diffraction data for $(H_2O)(14,28$-[1,3-diiminoisoindolinato]phthalocyaninato)Fe(III), in accordance with various embodiments.
Figure 5A:
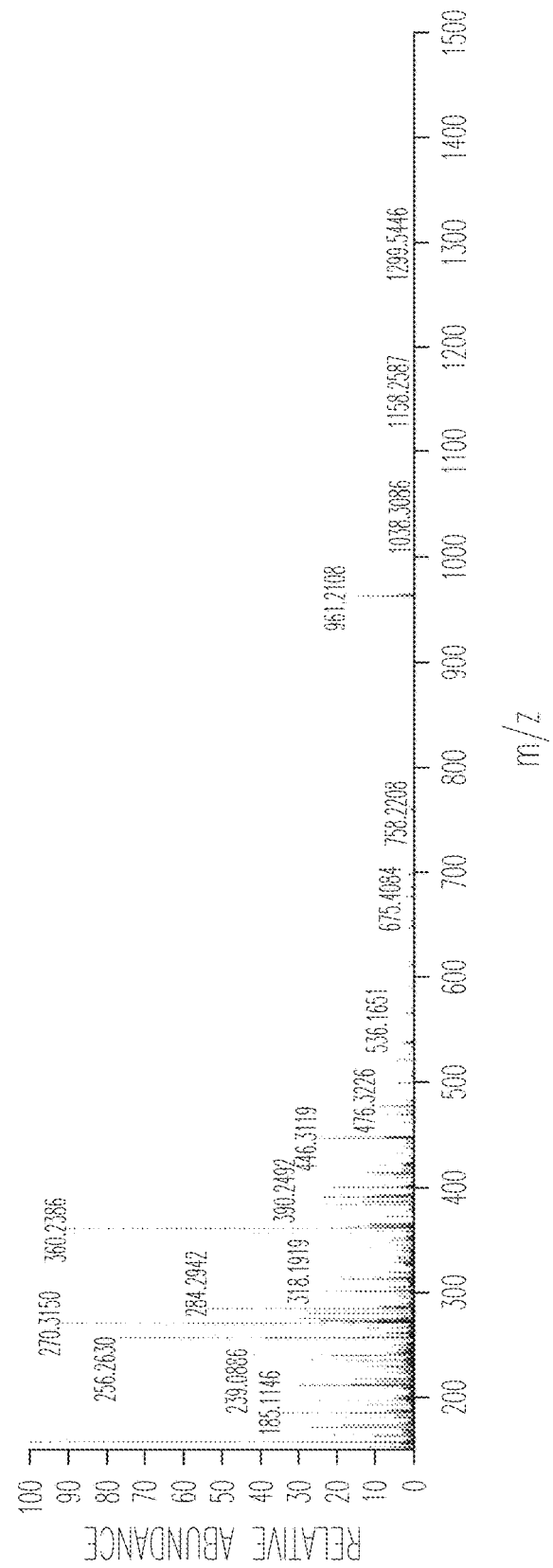
Figure 5B:
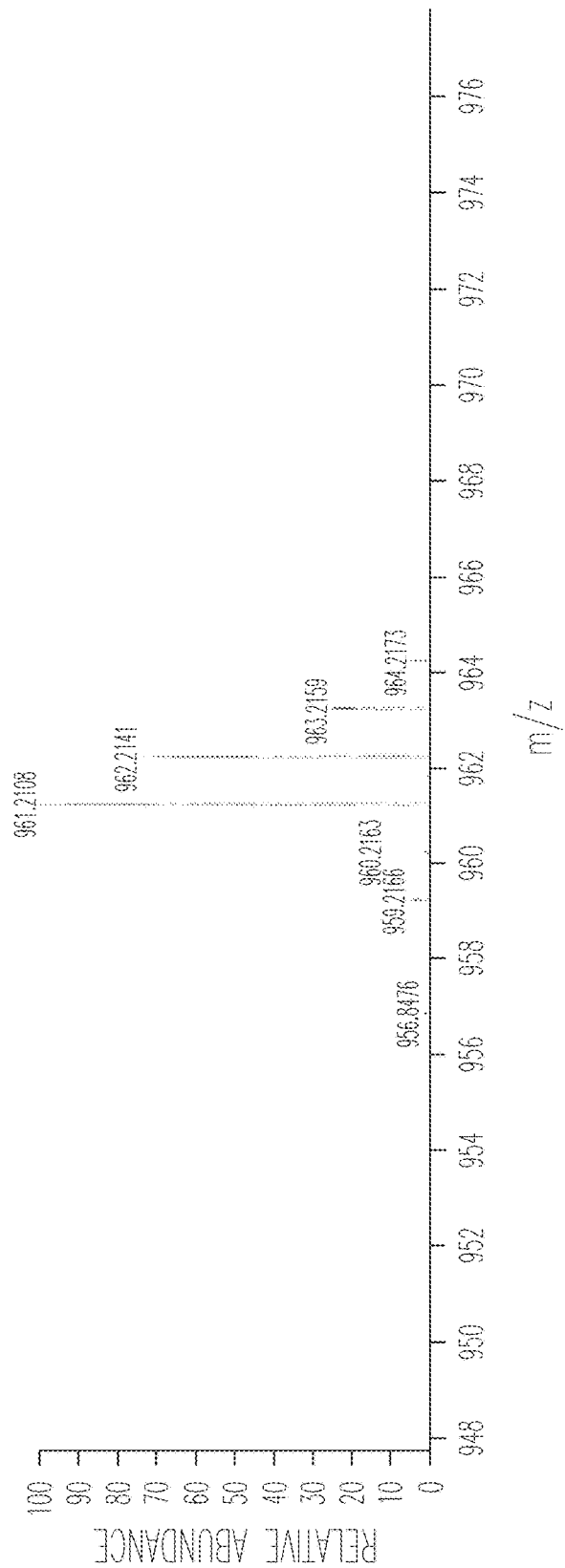
Figure 5C:
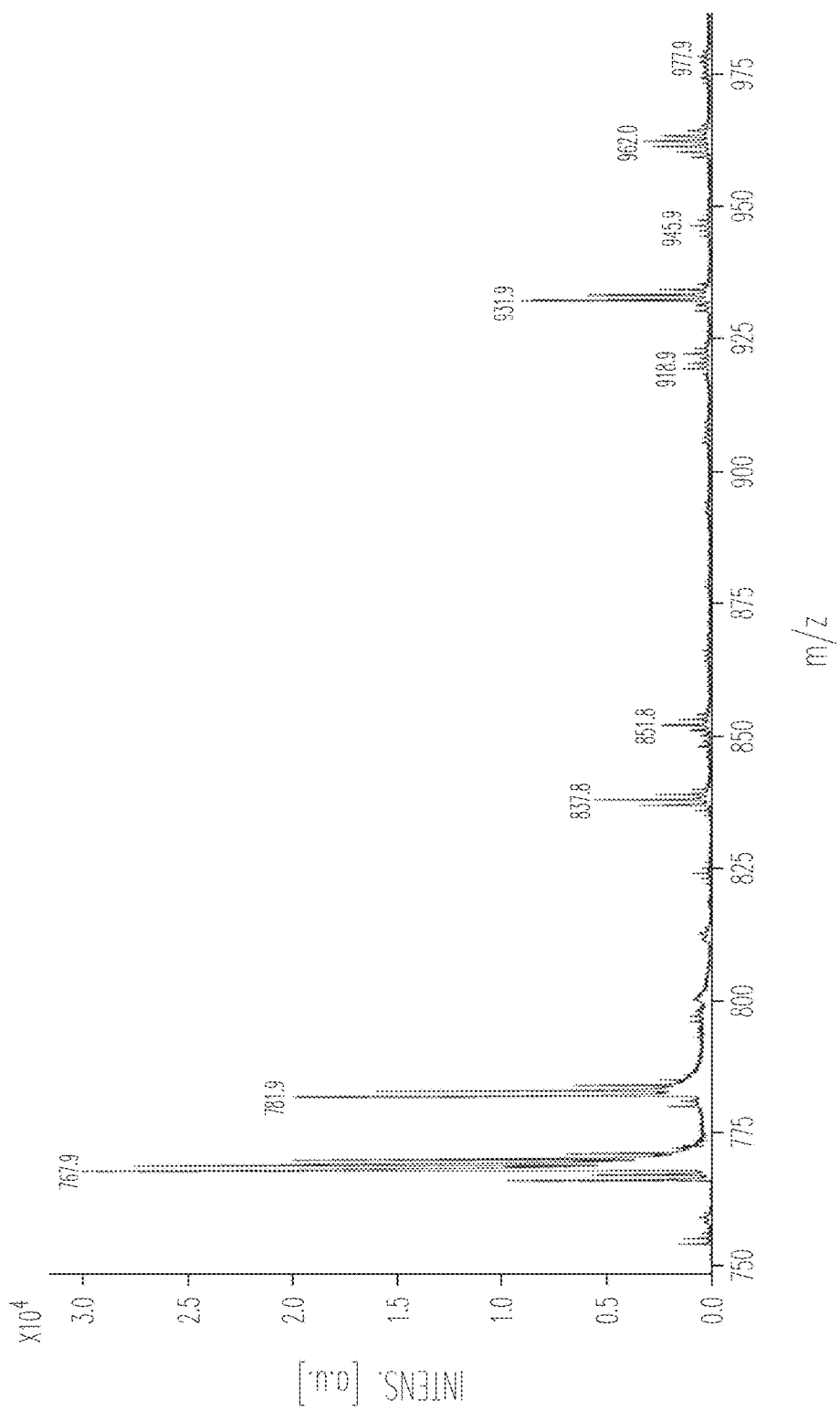

The catalyst employed in the reactions described here was prepared via a two step process. In the first step, 1,2-dicyanobenzene was allowed to react with iron(II) acetate under solvothermal conditions in methanol (130° C., 7 days), yielding a dark crystalline solid that was washed with methanol and dried. The structure of this material has been determined via single crystal X-ray methods to be (L)(14, 28-[1,3-diiminoisoindolinato]phthalocyaninato)Fe(III), or (L)(diiPc)Fe(III) 1, where L represents an axially coordinated monodentate ligand consisting of a mixture of methanol and water in an approximately 4:1 ratio, as reported earlier. Following isolation and washing of 1, the mixed axial ligand L was converted to 100% water by treatment with sulphuric acid. In a typical preparation, mixture 1 was stirred overnight in concentrated sulphuric acid resulting in a deep red solution that was diluted in water and carefully treated with 6M NaOH until the pH is approximately 2 and a dark solid precipitated. The converted product was then isolated as a powdery black solid following filtration on a glass frit and drying. The formulation of the solid thus obtained has been established as (H₂O)(diiPc)Fe(III) 2 via comparison of its IR spectral features to the known IR spectrum of 1, and by single crystal X-ray methods. The latter of these two techniques conclusively identified the identity of the axial ligand in 2 as 100% water with no compositional disorder. Single crystals of 2 were obtained by recrystallization of the solid as originally obtained in powder form from absolute ethanol via slow evaporation of the solvent. A structural drawing of 2 is presented in FIG. 3, where thermal ellipsoids are drawn at the 50% probability level. Further details regarding the structural determination for 2 and secondary (IR) characterization are presented as electronic supplementary information. Suitable elemental analysis for 2 cannot be obtained because of slow and incomplete solvent (ethanol) loss from the crystal lattice. Samples of 2 employed as catalysts in the oxidation reactions described below were obtained via filtration and drying without recrystallization, in order to avoid the presence of solvent that becomes entrained in solid 2 upon nearly complete evaporation of ethanolic solutions during recrystallization. Significantly, it was observed that 2 dissolves readily in a wide variety of non-aromatic primary and secondary alcohols other than methanol, in contrast to 1 which shows minimal to zero solubility in any alcohol lacking an aromatic group. FIG. 3 illustrates a molecular drawing generated from X-ray diffraction data for (H₂O)(14,28-[1,3-diiminoisoindolinato]phthalocyaninato)Fe(III) and co-crystallized ethanol molecules shown with 50% probability ellipsoids. All H atoms not involved in hydrogen bonding have been omitted for the sake of clarity.

Example 3-2

Oxidation Experiments

All oxidation reactions occurred in magnetically stirred round bottom flasks that were loosely capped with rubber septa under air. The primary oxidant in all reactions was 70% tert-butylhydroperoxide (TBHP) as an aqueous solution. Oxidations of 1-pentanol, 2-pentanol and cyclohexanol were carried out at room temperature. In the oxidation of 2,4-dimethyl-3-pentanol, the reaction mixture was heated to 63° C. in order to increase miscibility of the substrate with the oxidant solution. In the oxidation of 5-hydroxymethylfurfural, the reaction mixture was heated to 33° C. in order to melt the alcohol, which is a solid at room temperature. In all reactions, the catalyst was first dissolved in the substrate alcohol, then the oxidant solution was added in a single aliquat. Reaction times and substrate to oxidant ratios were varied in order to maximize TON and TOF. A summary of the optimized results of these experiments is presented in Table 1. At the conclusion of oxidation reactions, product mixtures were passed through short plugs of silica gel with copious diethyl ether in order to remove the catalyst from solution. Identification of products was accomplished by GC-MS through consideration of a combination of retention times as compared to those observed for authentic samples and fragmentation patterns observed in the corresponding mass spectra. Products were quantified against naphthalene as an internal standard.

TABLE 1

| Entry | Substrate | Product | Substrate:oxidant | Conditions | TON | TOF h⁻¹ |
|---|---|---|---|---|---|---|
| 1 | pentanol (OH) | pentanal (=O) | 3.2:1 | R.T., 15 min. | 320 | 1300 |
| 2 | 2-pentanol | 2-pentanone | 1.9:1 | R.T., 30 min. | 1200 | 2300 |
| 3 | 2,4-dimethyl-3-pentanol | 2,4-dimethyl-3-pentanone | 4.9:1 | 63° C., 6 min. | 520 | 5400 |
| 4 | cyclohexanol | cyclohexanone | 2.0:1 | R.T., 30 min. | 840 | 1700 |
| 5 | 5-hydroxymethylfurfural | 2,5-diformylfuran | 1.2:1 | 33° C., 6 min. | 440 | 4400 |
| 6 | benzyl alcohol | benzaldehyde | 22.0:1 | R.T., 30 min. | 370 | 730 |
| 7 | 1-phenylethanol | acetophenone | 22.9:1 | R.T., 30 min. | 580 | 1200 |

TABLE 1-continued

| Entry | Substrate | Product | Substrate:oxidant | Conditions | TON | TOF $h^{-1}$ |
|---|---|---|---|---|---|---|
| 8 | 4-chlorobenzyl alcohol | 4-chlorobenzaldehyde | 17.0:1 | 85° C., 30 min. | 840 | 1700 |
| 9 | diphenylmethanol | benzophenone | 13.0:1 | 75° C., 30 min. | 700 | 1400 |

Example 3-3

Results and Discussion: Oxidation of Primary and Secondary Non-Benzylic Alcohols The material 2 was observed to function as an active catalyst for the oxidation of five non-benzylic alcohols in the absence of added organic solvent with tert-butyl hydroperoxiede serving as the primary oxidant. This observation represents a significant extension of the general versatility of the (diiPc)Fe(III) moiety as a catalyst for organic oxidations. The results of the oxidation experiments are summarized in Table 1 (entries 1-5). For the purpose of comparison, and to highlight the versatility of the (diiPc)Fe(III) system in oxidation catalysis, some of the results of the catalytic oxidation of four benzylic alcohols that employed 1 are included to provide examples of reactions carried out under conditions that parallel those employed in reactions reported for the first time here as closely as possible in terms of reaction times and the primary oxidant employed (TBHP). The alcohol substrates chosen were selected with intent to demonstrate the utility of the diiPcFe(III) system with a diverse array of substrates. Included are results for the oxidations of secondary aliphatic alcohols (2-pentanol, 2,4-dimethyl-3-pentanol, and cyclohexanol), a primary aliphatic alcohol (1-pentanol), and a bifunctional primary allylic alcohol, 5-hydroxymethylfurfural. The last of these transformations (entry 5) is an important step in the production of value-added oxidized products from a biomass-sourced alcohol.

The results presented in entries 1-5 of Table 1 derive from experiments that were designed to maximize TON and TOF together for each substrate, as both favourable catalyst durability and reaction speed were sought to be demonstrated. In the optimization procedure reaction times and substrate were varied to oxidant ratios to provide maximal values for these metrics. In all cases, reaction times longer than those indicated in Table 1 resulted in greater TON values, but these enhancements came at the expense of TOF and indicated a slowing of the oxidation reactions over time. One possible reason for this observation is discussed briefly below. In a general sense, oxidations of secondary aliphatic alcohols to produce ketones (entries 2, 3, and 4) proceeded with greater TON values than either of the non-benzylic primary alcohols studied (entries 1 and 5). The TON and TOF values reported for the secondary aliphatic alcohols in two out of three cases were on the same order of magnitude as those for oxidation of two secondary benzylic alcohols (entries 7 and 9). The exception occurred in the oxidation of 2-pentanol to produce 2-pentanone, which proceeds with TON=1200, the highest value that was observed over a reaction period of thirty minutes. The fastest oxidation observed was of 2,4-dimethyl-3-pentanol (entry 3) for which TOF=5400 $h^{-1}$. While this rather impressive result may be due in part to the elevated reaction temperature (63° C.), it does constitute performance that is in terms of TOF alone superior to almost all of the homogeneous catalytic systems that function without added organic solvent. The oxidation of 4-hydroxymethylfurfural (entry 5) proceeded nearly as rapidly, producing 440 turnovers in only six minutes, corresponding to TOF=4400. No significant background reaction was observed for any of the transformations in entries 1-5 when these reactions were attempted in the absence of catalyst under otherwise analogous conditions.

Significantly, none of the primary alcohol oxidations resulted in the formation of any detectable amount of carboxylic acid. In the oxidation of 5-hydroxymethylfurfural no evidence was observed that either the pre-existing aldehyde functional group present in the substrate or the aldehyde group formed in the oxidation of the alcohol functional group were oxidized further to produce carboxylic acids. While reactions were examined in which hydrogen peroxide served as the primary oxidant for non-benzylic substrates, the observed results were vastly inferior to those presented in Table 1 in terms of all relevant metrics. This was presumably due at least in part to poor miscibility of aqueous hydrogen peroxide solution with the alcohol substrates under investigation. It is interesting to note that hydrogen peroxide was also found in most respects to give inferior performance to that observed for TBHP for benzylic alcohol oxidation.

Example 3-4

Results and Discussion: Evaluation of the diiPc Moiety as a General Alcohol Oxidation Catalyst Results for oxidation reactions catalyzed by 2 were, in a general sense, comparable to those observed in reactions for benzylic alcohols catalyzed by 1. Although observed TON values were nominally higher and turnover frequencies were significantly higher for the more recent experiments involving non-benzylic substrates, at least some of the apparent improvement in performance must be ascribed to higher ratios of oxidant to substrate. The decision to employ the higher relative amounts of oxidant was borne in part from a desire to improve TON and TOF. This decision was also taken in response to the observation that reactions of non-benzylic substrates proceeded very sluggishly and with low TON values when stoichiometries comparable to those previously employed were applied. Although the reason for this observation is not yet clear, it is quite reasonable to expect that higher oxidant concentrations were necessary for oxidations of non-benzylic substrates in order to decrease the likelihood that the axial position opposite the pentadentate diiPc ligand on the catalyst will become occupied by an alcohol substrate molecule at the completion of a catalytic cycle. Occupation of this coordination site by the alcohol substrates themselves could significantly decrease the solubility of the catalyst complex, given the very low solubility of 1, which bears mostly methanol ligands at this axial site, in non-aromatic alcohols. Regardless of the specific mechanism by which 2 functions as a catalyst in alcohol oxidation reactions, higher oxidant concentrations can favour further cycling of the catalyst over effective de-activation of the catalyst due to markedly decreased solubility as the axial ligand position becomes occupied by alcohol substrate.

The seemingly minor modification of 1 in which the monodentate axial ligand L was converted from a methanol-water mixture heavily favouring methanol to 100% water was obviously a vital factor in expanding the versatility of the diiPcFe(III) system. The solubility characteristics of 2 were surprising and it is not clear why the presence of only water as the axial monodentate ligand in 2 markedly increases solubility. This observation could result from the fact that water ligands posses two hydrogen bond donors available for interaction with the (non-aromatic) alcohol substrates, as opposed to only one in the case of methanol (or other alcohols). Indeed, the solid state structure of 2 determined via single crystal X-ray methods employing a crystal grown from ethanol solution includes two co-crystallized ethanol molecules that are hydrogen bonded to the axial water ligand, suggesting that similar interactions are likely to occur in alcohol solutions. This hydrogen bonding in the solid state is conclusively identified by O—O distances of 2.586(2) and 2.606(2) Å between the oxygen atom on water and the oxygen atoms on these ethanol molecules, and by H—O distances between the hydrogen atoms of the water ligand and the ethanol oxygen atoms of 1.75(1) and 1.78(1) Å. The solubility of 1 in benzylic alcohols is presumably the result of interactions of the aromatic rings in the metal complex with those in the substrates.

In most of these catalytic systems for solvent free oxidation of alcohols reaction times are undesirably long, which imply much lower degrees of rate enhancement than are evidenced by the turnover frequencies observed for the diiPcFe(III) moiety. Overall, the diiPcFe(III) system holds a significant advantage over many other catalytic systems that function in the absence added organic solvent in that diiPc complexes are very easily and inexpensively prepared. Further, in cases where primary alcohols are oxidized to aldehydes (entries 1, 5, 6 and 8 in Table 1) no evidence of over-oxidation to carboxylic acid is observed, demonstrating excellent chemoselectivity for (diiPc)Fe(III) in general.

The helmet phthalocyaninato iron(III) system, (diiPc)Fe (III), outperforms most other known homogeneous catalysts of a similar nature in terms of TON and TOF. The applicability of this system in oxidation reactions is now generalized to include both primary and secondary aliphatic alcohols and one bifunctional allylic alcohol. Excellent selectivity is observed in all cases. Continuing improvements in this promising system may be achieved by synthetic modifications on the diiPc ligand that impart further enhancements to catalyst solubility in substrates or water solubility, and/or superior stability in substrate alcohols Example 3-5

X-Ray Analysis

Single Crystal X-Ray Analysis of 2-Experimental: Data Collection:

A red crystal with approximate dimensions 0.08×0.08×0.08 mm$^3$ was selected under oil under ambient conditions and attached to the tip of a MiTeGen MicroMount©. The crystal was mounted in a stream of cold nitrogen at 100(1) K and centered in the X-ray beam by using a video camera. Crystal evaluation and data collection were performed on a Bruker Quazar SMART APEXII diffractometer with Mo $K_\alpha$ ($\lambda$=0.71073 Å) radiation and the diffractometer to crystal distance of 4.96 cm. Initial cell constants were obtained from three series of $\omega$ scans at different starting angles. Each series consisted of 12 frames collected at intervals of 0.5° in a 6° range about $\omega$ with the exposure time of 5 seconds per frame. The reflections were successfully indexed by an automated indexing routine built in the APEXII program suite. The final cell constants were calculated from a set of 9955 strong reflections from the actual data collection.

Data were collected by using the full sphere data collection routine to survey the reciprocal space to the extent of a full sphere to a resolution of 0.70 Å. A total of 111776 data were harvested by collecting 6 sets of frames with 0.5° scans in $\omega$ and $\varphi$ with exposure times of 20 sec per frame. These highly redundant datasets were corrected for Lorentz and polarization effects. The absorption correction was based on fitting a function to the empirical transmission surface as sampled by multiple equivalent measurements.

Single Crystal X-Ray Analysis of 2-Structure Solution and Refinement.

The systematic absences in the diffraction data were uniquely consistent for the space group P2$_1$/n that yielded chemically reasonable and computationally stable results of refinement. A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms not involved in hydrogen bonding were included in the structure factor calculation at idealized positions and were allowed to ride on the neighboring atoms with relative isotropic displacement coefficients. The O—H distances were refined with restraints, but the H atom positions were allowed to refine. There are also three molecules of solvent EtOH per Fe complex in the lattice. The final least-squares refinement of 577 parameters against 12032 data resulted in residuals R (based on F$^2$ for I≥2σ) and wR (based on F$^2$ for all data) of 0.0374 and 0.0969, respectively. The final difference Fourier map was featureless.

Summary-Crystal Data for $C_{46}H_{40}FeN_{11}O_4$ (M=866.74 g/mol): monoclinic, space group P2$_1$/n (no. 14), a=15.200(4) Å, b=13.875(4) Å, c=19.210(5) Å, β=104.532(11°), V=3922 (2) Å$^3$, Z=4, T=100.04 K, μ(MoKα)=0.448 mm$^{-1}$, Dcalc=1.468 g/cm$^3$, 111776 reflections measured (3.068°≤2Θ≤61.142°), 12032 unique ($R_{int}$=0.0541, $R_{sigma}$=0.0290) which were used in all calculations. The final R$_1$ was 0.0374 (I>2σ(I)) and wR$_2$ was 0.0969 (all data)

FIGS. 4A-M illustrate X-ray data for (H$_2$O)(14,28-[1,3-diiminoisoindolinato]phthalocyaninato)Fe(III), shown in Tables 2-9.

IR for 2 (KBr, cm$^{-1}$): 3421 (br), 1628.2 (m), 1563.6 (s), 1519.9 (s), 1471 (s), 1441.5 (s), 1397.6 (m), 1322.2 (m), 1295.6 (w), 1193.5 (m), 1100 (w), 1031.6 (w), 730.3 (s), 458.5 (br).

Mass spectrometry data for 2. Sample was isolated and purified via flash column and recrystallization from methylene chloride and methanol. Formula: $C_{60}H_{32}FeN_{11}O$ (4-cocrystalized MeOH molecules also). Molecular weight, without co-crystalized solvent=978.81.

Example 3-6

Compound 2, which had already been characterized via single crystal X-ray diffraction methods and secondarily by IR spectroscopy, has now been further characterized via electrospray ionization (ESI) mass spectrometry. FIGS. 5A-D illustrate mass spectrometry data for $(H_2O)(14,28$-[1,3-diiminoisoindolinato]phthalocyaninato)Fe(III), 2. Specifically, the mass spectrum obtained showed a peak at mass 961.2108, corresponding to the compound claimed after loss of the water ligand L and acquisition of a single proton during the course of ionization, having formula $[C_{60}H_{30}N_{11}FeH]^+$ for which the calculated mass is 961.2109. This agreement between observed and calculated masses is within 0.1 ppm. The loss of a water ligand from the claimed compound and acquisition of a proton during ionization is completely reasonable from a chemical standpoint. This observation constitutes definitive characterization of the claimed compound secondary to the already presented X-ray data.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method of purifying a catalyst, the method comprising:

contacting a catalyst composition with acid, the catalyst composition comprising a catalyst, to provide an acidified catalyst composition with the catalyst dissolved therein, the catalyst having the structure:

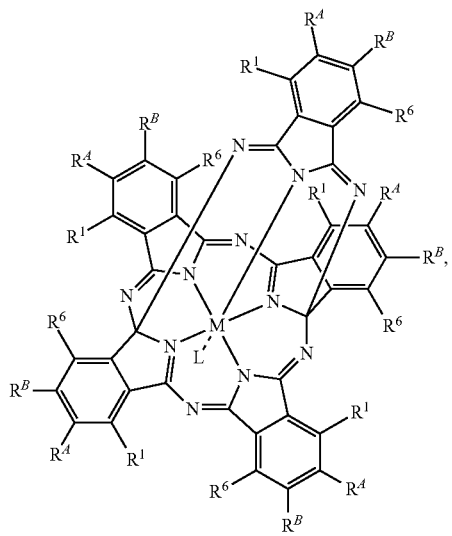

wherein
M is a metal,
axial ligand L is a solvent molecule,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

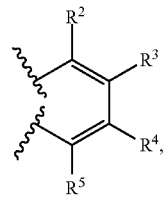

and
at each occurrence, $R^1$, $R^2$, $R^3$, $R^4$, $R^5$, and $R^6$ are each independently chosen from —H, halide, an organic group, and a hydrophilic group;

precipitating the catalyst; and
removing the precipitated catalyst from solution, to provide a purified catalyst.

Embodiment 2 provides the method of Embodiment 1, wherein the acid is one or more mineral acids.

Embodiment 3 provides the method of any one of Embodiments 1-2, wherein the acid is sulfuric acid.

Embodiment 4 provides the method of any one of Embodiments 1-3, wherein the acidified catalyst composition has a pH of about −3 to about 6.

Embodiment 5 provides the method of any one of Embodiments 1-4, wherein the acidified catalyst composition has a pH of about 0 to about 1.

Embodiment 6 provides the method of any one of Embodiments 1-5, wherein the catalyst is fully dissolved in the acidified catalyst composition.

Embodiment 7 provides the method of any one of Embodiments 1-6, wherein all materials in the acidified catalyst composition are fully dissolved.

Embodiment 8 provides the method of any one of Embodiments 1-7, further comprising separating any undissolved materials in the acidified catalyst composition from the acidified catalyst composition prior to the precipitating.

Embodiment 9 provides the method of any one of Embodiments 1-8, wherein the precipitating comprises at least partially neutralizing the acidified composition.

Embodiment 10 provides the method of Embodiment 9, wherein the at least partially neutralizing comprises bringing the acidified composition to a pH of about 0.5 to about 6.

Embodiment 11 provides the method of any one of Embodiments 9-10, wherein the at least partially neutralizing comprises bringing the acidified composition to a pH of about 1 to about 4.

Embodiment 12 provides the method of any one of Embodiments 9-11, wherein the at least partially neutralizing comprises contacting the acidified composition with a base.

Embodiment 13 provides the method of any one of Embodiments 9-12, wherein the at least partially neutralizing comprises contacting the acidified composition with at least one of NaOH and KOH.

Embodiment 14 provides the method of any one of Embodiments 1-13, wherein precipitating comprises diluting the acidified composition with water.

Embodiment 15 provides the method of Embodiment 14, wherein the diluting comprises diluting with water that has a volume of about 0.01 to about 100 times the volume of the acidified composition.

Embodiment 16 provides the method of any one of Embodiments 14-15, wherein the diluting comprises diluting with water that has a volume of about 2 to about 10 times the volume of the acidified composition.

Embodiment 17 provides the method of any one of Embodiments 1-16, wherein the removing comprises washing the precipitated catalyst with water.

Embodiment 18 provides the method of any one of Embodiments 1-17, further comprising recrystallizing the precipitated catalyst, to provide the purified catalyst.

Embodiment 19 provides the method of any one of Embodiments 1-18, further comprising recrystallizing the precipitated catalyst from ethanol, to provide the purified catalyst.

Embodiment 20 provides the method of any one of Embodiments 1-19, wherein the purified catalyst is about 95 wt % pure to about 100 wt % pure.

Embodiment 21 provides the method of any one of Embodiments 1-20, wherein the purified catalyst is greater than 98 wt % pure.

Embodiment 22 provides the method of any one of Embodiments 1-21, wherein M is a Group VIII or IX transition metal.

Embodiment 23 provides the method of any one of Embodiments 1-22, wherein M is chosen from Co and Fe.

Embodiment 24 provides the method of any one of Embodiments 1-23, wherein M is Fe.

Embodiment 25 provides the method of any one of Embodiments 1-24, wherein axial ligand L is chosen from MeOH and H$_2$O.

Embodiment 26 provides the method of any one of Embodiments 1-25, wherein axial ligand L is H$_2$O.

Embodiment 27 provides the method of any one of Embodiments 1-26, wherein at each occurrence, the hydrophilic group is chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted (C$_1$-C$_{50}$) hydrocarbyl ester thereof, and a combination thereof Embodiment 28 provides the method of any one of Embodiments 1-27, wherein at each occurrence, the hydrophilic group is —S(O)(O)OH.

Embodiment 29 provides the method of any one of Embodiments 1-28, wherein R$^A$ and R$^B$ have the structure:

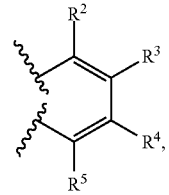

and wherein R$^1$, R$^2$, R$^3$, R$^4$, R$^5$, and R$^6$ are —H.

Embodiment 30 provides the method of any one of Embodiments 1-29, wherein R$^A$ and R$^B$ have the structure:

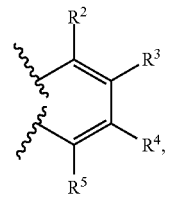

wherein

R$^1$ and R$^6$ are —H, and at each occurrence, R$^2$, R$^3$, R$^4$, and R$^5$ are independently chosen from —H and a hydrophilic group.

Embodiment 31 provides the method of Embodiment 30, wherein at one more occurrences at least one of R$^2$, R$^3$, R$^4$, and R$^5$ is a hydrophilic group.

Embodiment 32 provides the method of any one of Embodiments 1-31, wherein R$^A$ and R$^B$ have the structure:

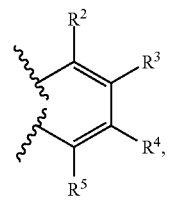

wherein

R$^1$ and R$^6$ are —H, and at each occurrence, R$^2$, R$^3$, R$^4$, and R$^5$ are independently chosen from —H and —S(O)(O)OH.

Embodiment 33 provides the method of Embodiment 32, wherein at one more occurrences at least one of R$^2$, R$^3$, R$^4$, and R$^5$ is —S(O)(O)OH.

Embodiment 34 provides the method of Embodiment 1-33, wherein R$^1$, R$^A$, R$^B$, and R$^6$ are —H.

Embodiment 35 provides the method of any one of Embodiments 1-34, wherein the catalyst has the structure:

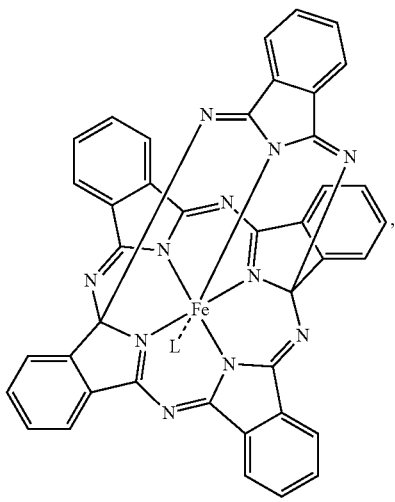

wherein axial ligand L is H$_2$O.

Embodiment 36 provides the method of any one of Embodiments 1-35, wherein about 0.001 wt % to about 99.999 wt % of the catalyst composition is the catalyst.

Embodiment 37 provides the method of any one of Embodiments 1-36, wherein the catalyst composition further comprises a secondary catalyst, wherein the secondary catalyst has a different structure than the catalyst, wherein the secondary catalyst has the structure:

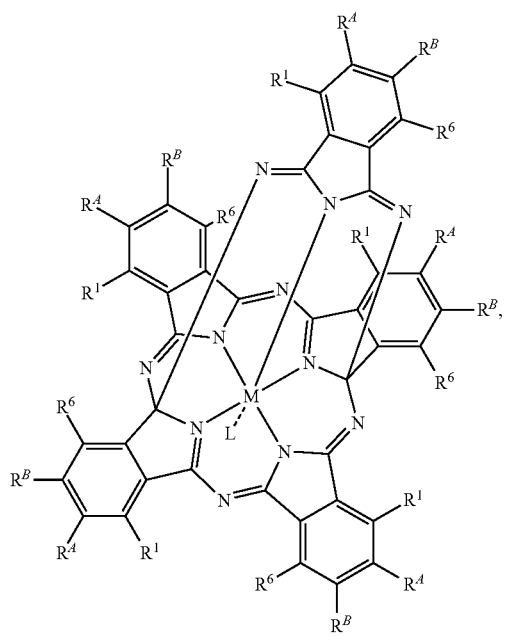

wherein
M is a metal,
axial ligand L is a solvent molecule,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

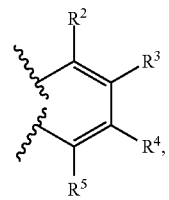

at each occurrence, $R^1$, $R^2$, $R^3$, $R^4$, $R^5$, and $R^6$ are each independently chosen from —H, halide, an organic group, and a hydrophilic group.

Embodiment 38 provides the method of Embodiment 37, wherein the secondary catalyst has the structure:

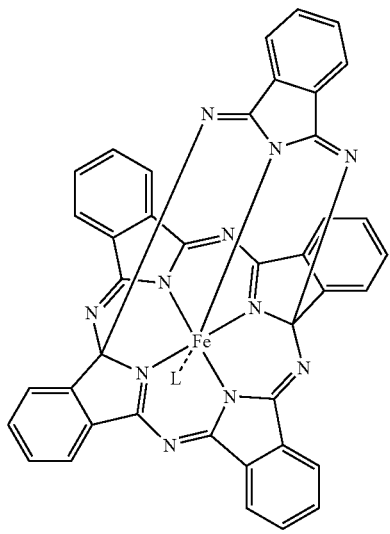

wherein axial ligand L is MeOH.

Embodiment 39 provides the method of any one of Embodiments 37-38, wherein 50 wt % to 100 wt % of the catalyst composition is the catalyst and the secondary catalyst.

Embodiment 40 provides the method of any one of Embodiments 37-39, wherein 100 wt % of the catalyst composition is the catalyst and the secondary catalyst.

Embodiment 41 provides the method of any one of Embodiments 37-40, wherein the purified catalyst is substantially free of the secondary catalyst.

Embodiment 42 provides the purified catalyst of any one of Embodiments 1-41.

Embodiment 43 provides a method of purifying a catalyst, the method comprising contacting a catalyst composition with acid, the catalyst composition comprising a catalyst, to provide an acidified catalyst composition having a pH of about 0 to about 1 with the catalyst dissolved therein, the catalyst having the structure:

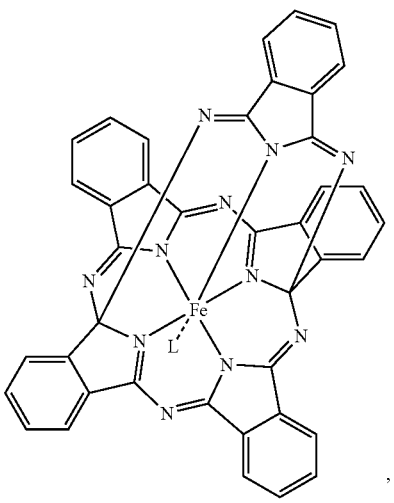

wherein axial ligand L is H₂O, wherein the catalyst composition further comprises a secondary catalyst having the structure:

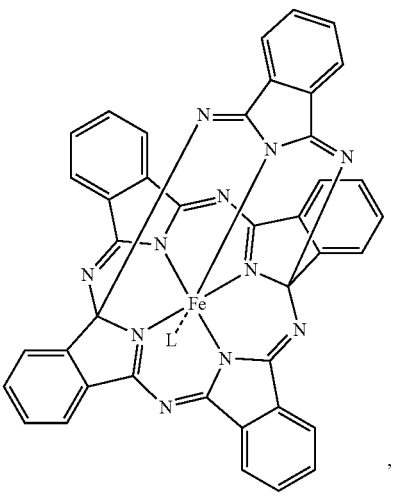

wherein L is MeOH;

precipitating the catalyst, comprising bringing the pH of the acidified composition to about 1 to about 4;

removing the precipitated catalyst from solution;

washing the precipitated catalyst with water; and recrystallizing the precipitated catalyst, to provide a purified catalyst.

Embodiment 44 provides a purified catalyst having the structure:

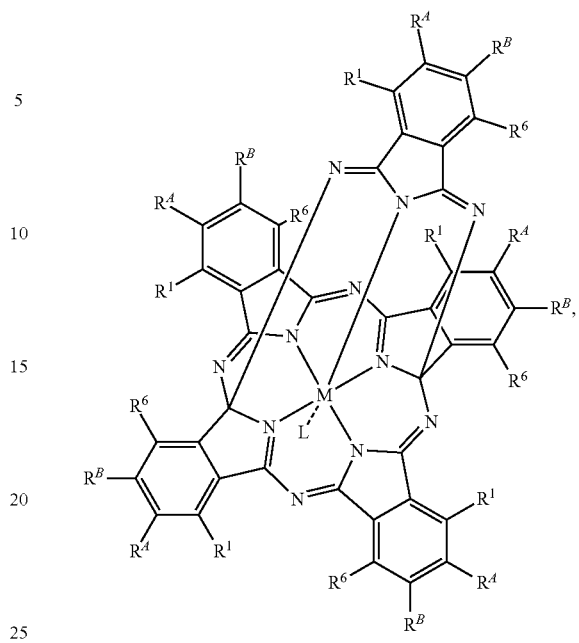

wherein

M is a metal, axial ligand L is a solvent molecule, at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

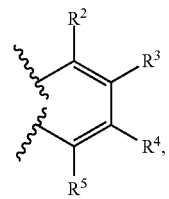

at each occurrence, $R^1$, $R^2$, $R^3$, $R^4$, $R^5$, and $R^6$ are each independently chosen from —H, halide, an organic group, and a hydrophilic group, and the purified catalyst is about 95 wt % pure to about 100 wt % pure.

Embodiment 45 provides the method of Embodiment 44, wherein M is a Group VIII or IX transition metal.

Embodiment 46 provides the purified catalyst of any one of Embodiments 44-45, wherein M is chosen from Co and Fe.

Embodiment 47 provides the purified catalyst of any one of Embodiments 44-46, wherein M is Fe.

Embodiment 48 provides the purified catalyst of any one of Embodiments 44-47, wherein axial ligand L is chosen from MeOH and H₂O.

Embodiment 49 provides the purified catalyst of any one of Embodiments 44-48, wherein axial ligand L is H₂O.

Embodiment 50 provides the purified catalyst of any one of Embodiments 44-49, wherein at each occurrence, the hydrophilic group is chosen from —C(O)OH, —O—C(O)OH, —P(O)(OH)₂, —OP(O)(OH)₂, —S(O)(O)OH, —OS (O)(O)OH, a salt thereof, a substituted or unsubstituted ($C_1$-$C_{50}$)hydrocarbyl ester thereof, and a combination thereof.

Embodiment 51 provides the purified catalyst of any one of Embodiments 44-50, wherein at each occurrence, the hydrophilic group is —S(O)(O)OH.

Embodiment 52 provides the purified catalyst of any one of Embodiments 44-51, wherein $R^A$ and $R^B$ have the structure:

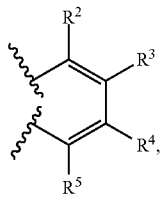

and
wherein $R^1$, $R^2$, $R^3$, $R^4$, $R^5$, and $R^6$ are —H.

Embodiment 53 provides the purified catalyst of any one of Embodiments 44-52, wherein $R^A$ and $R^B$ have the structure:

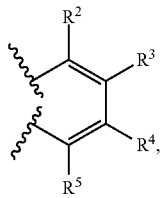

wherein
$R^1$ and $R^6$ are —H, and
at each occurrence, $R^2$, $R^3$, $R^4$, and $R^5$ are independently chosen from —H and a hydrophilic group.

Embodiment 54 provides the purified catalyst of Embodiment 53, wherein at one more occurrences at least one of $R^2$, $R^3$, $R^4$, and $R^5$ is a hydrophilic group.

Embodiment 55 provides the purified catalyst of any one of Embodiments 44-54, wherein $R^A$ and $R^B$ have the structure:

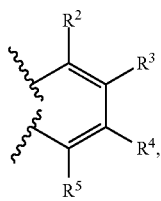

wherein
$R^1$ and $R^6$ are —H, and
at each occurrence, $R^2$, $R^3$, $R^4$, and $R^5$ are independently chosen from —H and —S(O)(O)OH.

Embodiment 56 provides the purified catalyst of Embodiment 55, wherein at one more occurrences at least one of $R^2$, $R^3$, $R^4$, and $R^5$ is —S(O)(O)OH.

Embodiment 57 provides the purified catalyst of any one of Embodiments 44-56, wherein $R^1$, $R^4$, $R^B$, and $R^6$ are —H.

Embodiment 58 provides the purified catalyst of any one of Embodiments 44-57, wherein the catalyst has the structure:

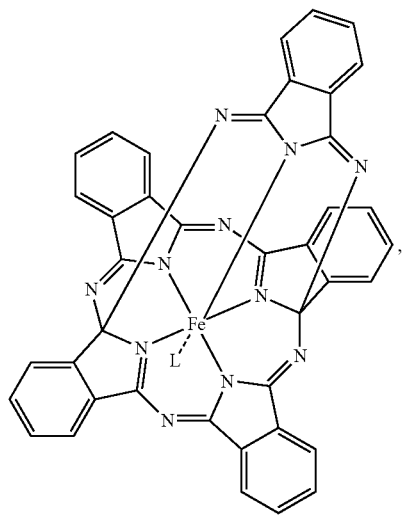

wherein axial ligand L is $H_2O$.

Embodiment 59 provides a method of oxidation, comprising:
contacting an oxidizable starting material with the catalyst of Embodiment 44 and an oxidant, to provide an oxidized product.

Embodiment 60 provides the method of Embodiment 59, wherein the contacting to provide an oxidized product is carried out under solvent-free conditions.

Embodiment 61 provides the method of any one of Embodiments 59-60, wherein the oxidant is chosen from tert-butylhydroperoxide, hydrogen peroxide, and combinations thereof Embodiment 62 provides the method of any one of Embodiments 59-61, wherein the oxidizable starting material is a substituted or unsubstituted ($C_1$-$C_{50}$)hydrocarbyl alcohol.

Embodiment 63 provides the method of any one of Embodiments 59-62, wherein the oxidizable starting material is chosen from 2-pentanol, 1-pentanol, and 2,4-dimethyl-3-pentanol.

Embodiment 64 provides the method of any one of Embodiments 59-63, wherein during the contacting to provide the oxidized product, the catalyst has a turnover number of about 200 to about 10,000.

Embodiment 65 provides the method of any one of Embodiments 59-64, wherein during the contacting to provide the oxidized product, the catalyst has a turnover number of about 300 to about 1,000.

Embodiment 66 provides the method of any one of Embodiments 59-65, wherein during the contacting to provide the oxidized product, the catalyst has a turnover frequency of about 500 $h^{-1}$ to about 20,000 $h^{-1}$.

Embodiment 67 provides the method of any one of Embodiments 59-66, wherein during the contacting to provide the oxidized product, the catalyst has a turnover frequency of about 1,000 $h^{-1}$ to about 3,000 $h^{-1}$.

Embodiment 68 provides a purified catalyst having the structure:

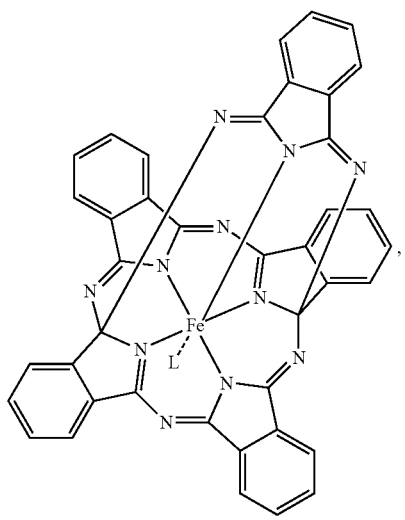

wherein axial ligand L is $H_2O$, and the purified catalyst is about 95 wt % pure to about 100 wt % pure.

Embodiment 69 provides a catalyst having the structure:

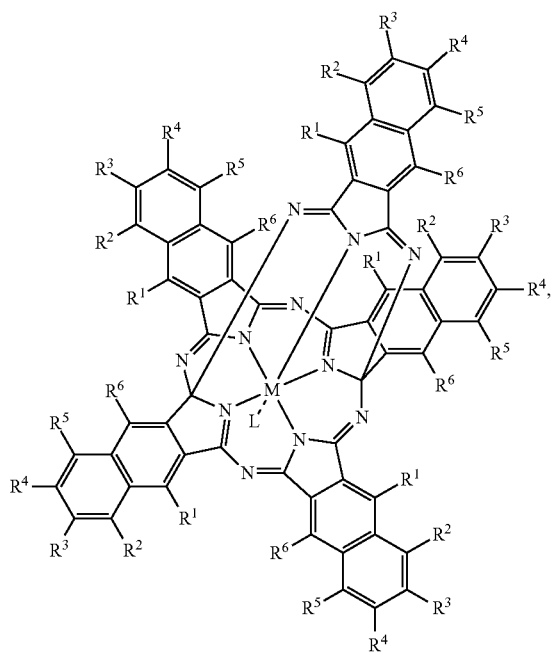

wherein

M is a metal,

L is a solvent molecule, and at each occurrence, $R^1$, $R^2$, $R^3$, $R^4$, $R^5$, and $R^6$ are independently chosen from —H, halide, an organic group, and a hydrophilic group.

Embodiment 70 provides the catalyst of Embodiment 69, wherein $R^1$ and $R^6$ are —H, and at each occurrence, $R^2$, $R^3$, $R^4$, and $R^5$ are independently chosen from —H and a hydrophilic group.

Embodiment 71 provides the catalyst of any one of Embodiments 69-70, wherein $R^1$ and $R^6$ are —H, and at each occurrence, $R^2$, $R^3$, $R^4$, and $R^5$ are independently chosen from —H and —S(O)(O)OH.

Embodiment 72 provides the catalyst of any one of Embodiments 69-71, wherein $R^1$ and $R^6$ are —H, at each occurrence, $R^2$, $R^3$, $R^4$, and $R^5$ are independently chosen from —H and a hydrophilic group, and at one more occurrences at least one of $R^2$, $R^3$, $R^4$, and $R^5$ is a hydrophilic group.

Embodiment 73 provides the catalyst of any one of Embodiments 69-72, wherein $R^1$ and $R^6$ are —H, at each occurrence, $R^2$, $R^3$, $R^4$, and $R^5$ are independently chosen from —H and a hydrophilic group, and at one more occurrences at least one of $R^2$, $R^3$, $R^4$, and $R^5$ is a —S(O)(O)OH.

Embodiment 74 provides a method of oxidation, comprising:

contacting an oxidizable starting material with the catalyst of any one of Embodiments 69-73 and an oxidant, to provide an oxidized product.

Embodiment 75 provides the method of Embodiment 74, wherein the contacting to provide an oxidized product is carried out under solvent free conditions.

Embodiment 76 provides the method of any one of Embodiments 74-75, wherein the oxidizable starting material is a substituted or unsubstituted ($C^1$-$C_{50}$)hydrocarbyl alcohol.

Embodiment 77 provides the method of any one of Embodiments 74-76, wherein the oxidizable starting material is chosen from 2-pentanol, 1-pentanol, and 2,4-dimethyl-3-pentanol.

Embodiment 78 provides a method of forming a catalyst, comprising forming the catalyst of Embodiment 69-73.

Embodiment 79 provides a method of forming a derivatized catalyst, comprising adding a hydrophilic group to the catalyst of any one of Embodiments 69-73.

Embodiment 80 provides a method of oxidation, comprising contacting an oxidizable starting material, the derivatized catalyst of Embodiment 79, an oxidant, and water, to form an oxidized product.

Embodiment 81 provides a method of forming a derivatized catalyst, comprising sulfonating the catalyst of any one of Embodiments 69-73.

Embodiment 82 provides a catalyst having the structure:

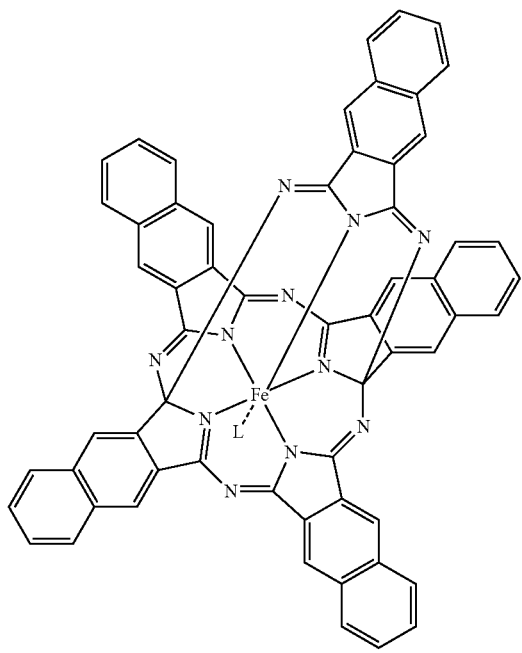

wherein L is H₂O.

Embodiment 83 provides a catalyst having the structure:

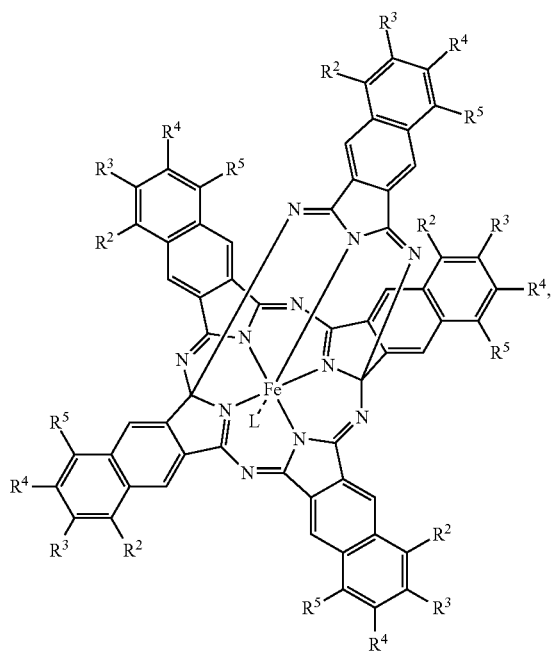

wherein
L is water,
at each occurrence $R^2$, $R^3$, $R^4$, and $R^5$ are independently chosen from —H and —S(O)(O)OH, and
at one or more occurrences at least one of $R^2$, $R^3$, $R^4$, and $R^5$ is —S(O)(O)OH.

Embodiment 84 provides the catalyst or method of any one or any combination of Embodiments 1-83 optionally configured such that all elements or options recited are available to use or select from.

What is claimed is:

1. A method of purifying a catalyst, the method comprising:
contacting a catalyst composition with acid, the catalyst composition comprising a catalyst, to provide an acidified catalyst composition with the catalyst dissolved therein, the catalyst having the structure:

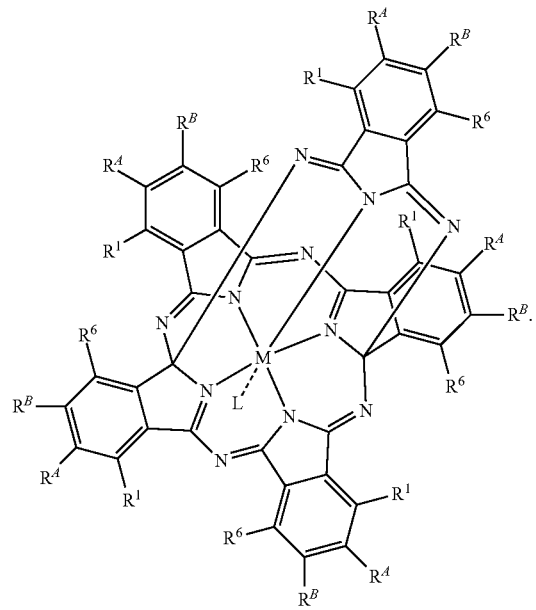

wherein
M is a metal,
axial ligand L is a solvent molecule,
at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

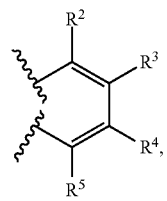

and
at each occurrence, $R^1$, $R^2$, $R^3$, $R^4$, $R^5$, and $R^6$ are each independently chosen from —H, halide, an organic group, and a hydrophilic group;
precipitating the catalyst; and
removing the precipitated catalyst from solution, to provide a purified catalyst.

2. The method of claim 1, wherein the precipitating comprises at least partially neutralizing the acidified composition.

3. The method of claim 1, wherein the removing comprises washing the precipitated catalyst with water.

4. The method of claim 1, wherein the purified catalyst is about 95 wt% pure to about 100 wt% pure.

5. The method of claim 1, wherein axial ligand L is chosen from MeOH and $H_2O$.

6. The method of claim 1, wherein at one more occurrences at least one of $R^2$, $R^3$, $R^4$, and $R^5$ is a hydrophilic group, wherein at each occurrence, the hydrophilic group is chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted $(C_1-C_{50})$hydrocarbyl ester thereof, and a combination thereof.

7. The method of claim 1, wherein at one more occurrences at least one of $R^2$, $R^3$, $R^4$, and $R^5$ is —S(O)(O)OH.

8. The method of claim 1, wherein the catalyst has the structure:

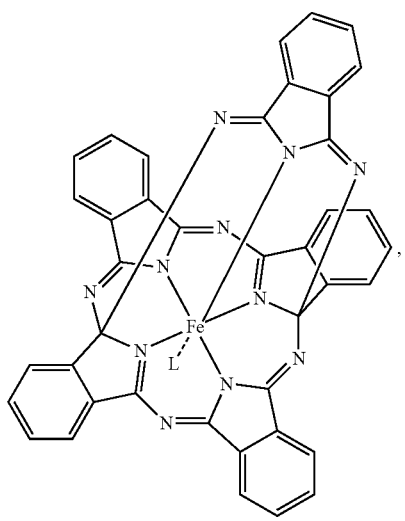

wherein axial ligand L is $H_2O$.

9. The method of claim 1, wherein the catalyst composition further comprises a secondary catalyst, wherein the secondary catalyst has a different structure than the catalyst, wherein the secondary catalyst has the structure:

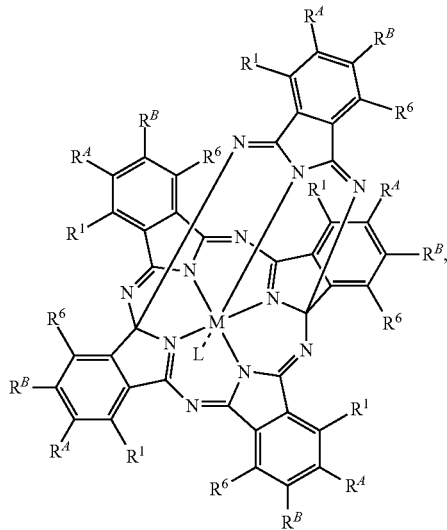

wherein

M is a metal, axial ligand L is a solvent molecule, at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

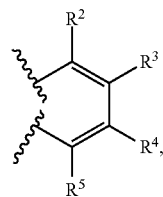

at each occurrence, $R^1$, $R^2$, $R^3$, $R^4$, $R^5$, and $R^6$ are each independently chosen from —H, halide, an organic group, and a hydrophilic group.

10. The method of claim 9, wherein the secondary catalyst has the structure:

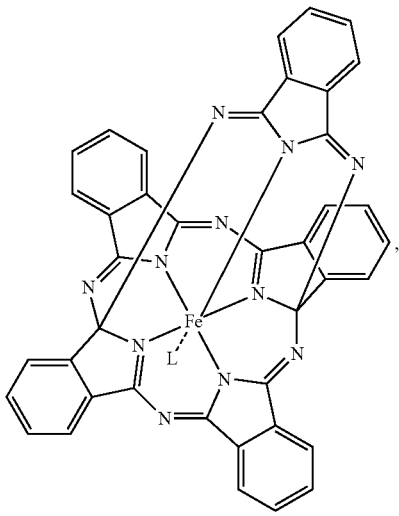

wherein axial ligand L is MeOH.

11. A purified catalyst having the structure:

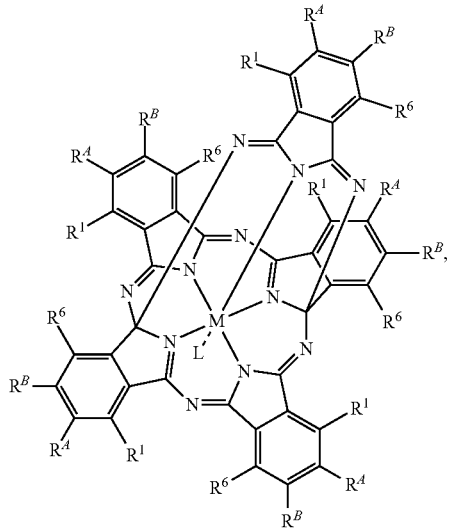

wherein

M is a metal, axial ligand L is a solvent molecule, at each occurrence, $R^A$ and $R^B$ are independently chosen from —H, halide, an organic group, and a hydrophilic group, or $R^A$ and $R^B$ together form a fused aromatic ring with the ring upon which $R^A$ and $R^B$ are substituted, $R^A$ and $R^B$ together having the structure:

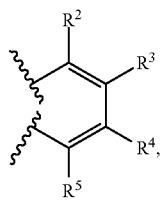

at each occurrence, $R^1$, $R^2$, $R^3$, $R^4$, $R^5$, and $R^6$ are each independently chosen from —H, halide, an organic group, and a hydrophilic group, wherein at each occurrence, the hydrophilic group is independently chosen from —C(O)OH, —O—C(O)OH, —P(O)(OH)$_2$, —OP(O)(OH)$_2$, —S(O)(O)OH, —OS(O)(O)OH, a salt thereof, a substituted or unsubstituted ($C_1$-$C_{50}$)hydrocarbyl ester thereof, and a combination thereof, and the purified catalyst is about 95 wt% pure to about 100 wt% pure.

12. The purified catalyst of claim 11, wherein axial ligand L, is chosen from MeOH and H$_2$O.

13. The purified catalyst of claim 11, wherein at one more occurrences at least one of $R^2$, $R^3$, $R^4$, and $R^5$ is —S(O)(O)OH.

14. The purified catalyst of claim 11, wherein the catalyst has the structure:

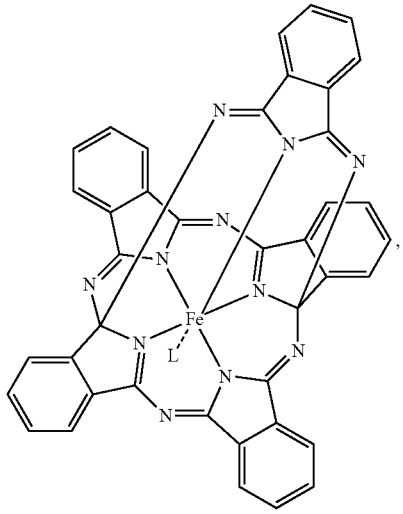

wherein axial ligand L is H$_2$O.

15. A method of oxidation, comprising:

contacting an oxidizable starting material with the catalyst of claim 11 and an oxidant, to provide an oxidized product, wherein the oxidizable starting material is a substituted or unsubstituted ($C_1$-$C_{50}$)hydrocarbyl alcohol.

16. A catalyst having the structure:

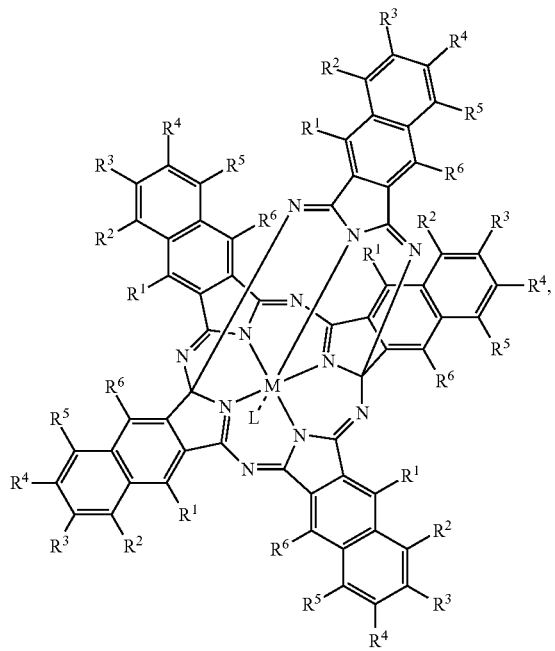

wherein

M is a metal,

L is a solvent molecule, and at each occurrence, $R^1$, $R^2$, $R^3$, $R^4$, $R^5$, and $R^6$ are independently chosen from —H, halide, an organic group, and a hydrophilic group.

17. A method of oxidation, comprising:

contacting an oxidizable starting material with the catalyst of claim 16 and an oxidant, to provide an oxidized product, wherein the oxidizable starting material is a substituted or unsubstituted $(C_1-C_{50})$hydrocarbyl alcohol.

18. The method of claim 17, wherein the contacting to provide an oxidized product is carried out under solvent-free conditions.

19. The purified catalyst of claim 11, wherein at least one of $R^A$, $R^B$, $R^1$, $R^2$, $R^3$, $R^4$, $R^5$ and $R^6$ is a hydrophilic group.

* * * * *